United States Patent
Sasai et al.

(10) Patent No.: US 12,091,680 B2
(45) Date of Patent: *Sep. 17, 2024

(54) METHOD FOR DIFFERENTIATION INDUCTION IN CULTURED STEM CELLS

(71) Applicants: RIKEN, Wako (JP); SUMITOMO CHEMICAL COMPANY, LIMITED, Tokyo (JP)

(72) Inventors: Yoshiki Sasai, Kobe (JP); Mototsugu Eiraku, Kobe (JP)

(73) Assignees: RIKEN, Wako (JP); Sumitomo Chemical Company, Limited, Tokyo (JP)

(*) Notice: Subject to any disclaimer, the term of this patent is extended or adjusted under 35 U.S.C. 154(b) by 867 days.

This patent is subject to a terminal disclaimer.

(21) Appl. No.: 17/063,139

(22) Filed: Oct. 5, 2020

(65) Prior Publication Data

US 2021/0115399 A1   Apr. 22, 2021

Related U.S. Application Data

(63) Continuation of application No. 13/508,303, filed as application No. PCT/JP2010/070163 on Nov. 5, 2010, now Pat. No. 10,793,830.

(60) Provisional application No. 61/258,439, filed on Nov. 5, 2009.

(51) Int. Cl.
*C12N 5/0789* (2010.01)
*C12N 5/079* (2010.01)
*C12N 5/0797* (2010.01)

(52) U.S. Cl.
CPC .......... *C12N 5/0621* (2013.01); *C12N 5/0623* (2013.01); *C12N 2500/90* (2013.01); *C12N 2501/16* (2013.01); *C12N 2506/02* (2013.01); *C12N 2533/52* (2013.01)

(58) Field of Classification Search
CPC ............... C12N 5/0621; C12N 5/0623; C12N 2500/90; C12N 2501/16; C12N 2506/02; C12N 2533/52; A61P 27/02
See application file for complete search history.

(56) References Cited

U.S. PATENT DOCUMENTS

| | | |
|---|---|---|
| 2003/0068819 A1 | 4/2003 | Zhang et al. |
| 2005/0095702 A1 | 5/2005 | Alam et al. |
| 2006/0211109 A1 | 9/2006 | Totey et al. |
| 2006/0252148 A1 | 11/2006 | Kurosawa et al. |
| 2008/0044901 A1 | 2/2008 | Sasai et al. |
| 2010/0105137 A1 | 4/2010 | Takahashi et al. |
| 2011/0027333 A1 | 2/2011 | Idelson et al. |
| 2011/0091869 A1 | 4/2011 | Sasai et al. |
| 2011/0274662 A1 | 11/2011 | Malcuit et al. |
| 2019/0218513 A1 | 7/2019 | Sasai et al. |

FOREIGN PATENT DOCUMENTS

| | | |
|---|---|---|
| EP | 1068295 A1 | 1/2001 |
| EP | 1783205 A1 | 5/2007 |
| EP | 2128244 A1 | 12/2009 |
| JP | 2002-517982 A | 6/2002 |
| JP | 2003-055402 A | 2/2003 |
| JP | 2004-229523 A | 8/2004 |
| JP | 2004-254622 A | 9/2004 |
| JP | 2004-305014 A | 11/2004 |
| JP | 2005-261365 A | 9/2005 |
| JP | 2006-055069 A | 3/2006 |
| JP | 2006-521807 A | 9/2006 |
| JP | 2007-520207 A | 7/2007 |
| JP | 2008-099662 A | 5/2008 |
| WO | WO 1999/053021 A1 | 10/1999 |
| WO | WO 2005/001019 A1 | 1/2005 |
| WO | WO 2005/123902 A1 | 12/2005 |
| WO | WO 2008/035110 A1 | 3/2008 |
| WO | WO 2008/087917 A1 | 7/2008 |
| WO | WO 2008/129554 A1 | 10/2008 |

OTHER PUBLICATIONS

Mao et al. "Rewiring the retinal ganglion cell gene regulatory network: Neurod1 promotes retinal ganglion cell fate in the absence of Math5." Development (2008) 135 (20): 3379-3388. (Year: 2008).*
Cardozo et al. "Optic cup morphogenesis across species and related inborn human eye defects." Development. Jan. 15, 2023; 150(2): dev200399. (Year: 2023).*
Buono et al. "Analysis of gene networkbifurcation during opticcup morphogenesis inzebrafish" Nature Communications vol. 12, Article No. 3866 (2021) (Year: 2021).*
Zhang et al. "Nuclear receptor TLX prevents retinal dystrophy and recruits the corepressor atrophin." Genes Dev. May 15, 2006; 20(10): 1308-1320. (Year: 2006).*
Meyer et al. "Modeling early retinal development with human embryonic and induced pluripotent stem cells" Proc Natl Acad Sci U S A.Sep. 29, 2009;106(39):16698-703 (Year: 2009).*
Brown et al. "Math5 is required for retinal ganglion cell and optic nerve formation." Development .Jul. 2001;128(13):2497-508 (Year: 2001).*
Levine et al. "Cell-intrinsic regulators of proliferation in vertebrate retinal progenitors."Semin Cell Dev Biol . Feb. 2004; 15(1):63-74. (Year: 2004).*
Carpenedo et al., "Rotary Suspension Culture Enhances the Efficiency, Yield, and Homogeneity of Embryoid Body Differentiation," *Stem Cells*, 25: 2224-2234 (2007).
Colas et al., "Towards a Cellular and Molecular Understanding of Neurulation," *Developmental Dynamics*, 221: 117-145 (2001).
Crawford et al., "The Notch Response Inhibitor DAPT Enhances Neuronal Differentiation in Embryonic Stem Cell-Derived Embryoid Bodies Independently of Sonic Hedgehog Signaling," *Developmental Dynamics*, 236: 886-892 (2007).
Eiraku et al., "Self-Organized Formation of Polarized Cortical Tissues from ESCs and Its Active Manipulation by Extrinsic Signals," *Cell Stem Cell*, 3(5): 519-532 (Nov. 6, 2008).

(Continued)

*Primary Examiner* — Titilayo Moloye
(74) *Attorney, Agent, or Firm* — Leydig, Voit & Mayer, Ltd.

(57) ABSTRACT

Provided is a method of inducing the differentiation of a stem cell into nerve progenitor cells, comprising the step (1) of forming homogenous aggregates of stem cells in a serum-free medium (1) and the step (2) of suspension-culturing the homogenous aggregates of stem cells in the presence of a basement membrane reference standard.

13 Claims, 11 Drawing Sheets

(56) References Cited

OTHER PUBLICATIONS

Eiraku et al., "Self-organizing optic-cup morphogenesis in three-dimensional culture," *Nature*, 472: 51-56 (2011).
Eiraku et al., "Mouse embryonic stem cell culture for generation of three-dimensional retinal and cortical tissues," *Nature Protocols*, 7(1): 69-79 (2012).
Ezekiel et al., "Single embryoid body formation in a multi-well plate," *Electronic Journal of Biotechnology*, 10(2): 328-335 (Apr. 15, 2007).
Farnsworth et al., "Directed Neural Differentiation of Induced Pluripotent Stem Cells from Nonhuman Primates," *Exp. Biol. Med.* (Maywood), 238(3): 276-284 (Mar. 1, 2013).
Fujiwara et al., "Regulation of Mesodermal Differentiation of Mouse Embryonic Stem Cells by Basement Membranes," *Journal of Biological Chemistry*, 282(40): 29701-29711 (Oct. 5, 2007).
Gonzalez-Cordero et al., "Photoreceptor precursors derived from three-dimensional embryonic stem cell cultures integrate and mature within adult degenerate retina," *Nat. Biotechnol.*, 31(8): 741-747 (2013).
Hirami et al., "Generation of retinal cells from mouse and human induced pluripotent stem cells," *Neuroscience Letters*, 458: 126-131 (2009).
Ikeda et al., "Generation of $Rx^+/Pax6^+$ neural retinal precursors from embryonic stem cells," *Proc. Natl. Acad. Sci. USA.*, 102(32): 11331-11336 (Aug. 9, 2005).
Ikeda et al., "In vitro differentiation of telencephalic precursors and neural retinal precursors from ES cells," *Jikken-igaku*, 24: 188-194 (2006).
Intarapat et al., "Chick stem cells: Current progress and future prospects," *Stem Cell Res.*, 11(3): 1378-1392 (2013).
Kadoshima et al., "Self-organization of axial polarity, inside-out layer pattern, and species-specific progenitor dynamics in human ES cell-derived neocortex," *Proc. Natl. Acad. Sci. USA*, 110(50): 20284-20289 (2013).
Krencik et al., "A cellular star atlas: using astrocytes from human pluripotent stem cells for disease studies," *Frontiers in Cellular Neuroscience*, 7: Article 25 (Mar. 14, 2013).
Kurosawa et al., "Novel Culture Technique for Formation of Mouse ES Cell Embryoid Body," *Department of Engineering, University of Yamanashi, Research Report*, 52: 23-29 (2003).
Kurosawa, "Methods for Inducing Embryoid Body Formation: In Vitro Differentiation System of Embryonic Stem Cells," *Journal of Bioscience and Bioengineering*, 103(5): 389-398 (2007).
Kuwahara et al., "Generation of a ciliary margin-like stem cell niche from self-organizing human retinal tissue," *Nature Communications*, 6: 6286 (2015).
Lamba et al., "Efficient generation of retinal progenitor cells from human embryonic stem cells," *Proc. Natl. Acad. Sci. USA*, 103(34): 12769-12774 (2006).
Lavial et al., "Chicken embryonic stem cells as a non-mammalian embryonic stem cell model," *Dev. Growth Differ.*, 52(1): 101-114 (2010).
Lee et al., "A Hollow Sphere Soft Lithography Approach for Long-Term Hanging Drop Methods," *Tissue Engineering: Part C*, 15(00): 1-11 (Aug. 3, 2009).
Ma et al., "Bioinformatic analysis of the four transcription factors used to induce pluripotent stem cells," *Cytotechnology.*, 66(6): 967-978. (2014).
Mariani et al., "Modeling Human Cortical Development in Vitro Using Induced Pluripotent Stem Cells," *Proc. Natl. Acad. Sci. USA*, 109(31): 12770-12775 (Jul. 31, 2012).
Moeller et al., "A microwell array system for stem cell culture," *Biomaterials*, 29(6): 752-763 (2008).
Muguruma et al., "Chapter 2: Clinical Application of Stem Cells—2. Human ES Cells and Neural Differentiation," *Experimental Medicine*, 26(5): 733-739 (Mar. 20, 2008).
Muguruma et al., "Ontogeny-recapitulating generation and tissue integration of ES cell-derived Purkinje cells," *Nat. Neurosci.*, 13(10): 1171-1180 and Online Methods (2010).
Muguruma et al., "Self-Organization of Polarized Cerebellar Tissue in 3D Culture of Human Pluripotent Stem Cells," *Cell Rep.*, 10(4): 537-550 (2015).
Nakano et al., "Self-Formation of Optic Cups and Storable Stratified Neural Retina from Human ESCs," *Cell Stem Cell*, 10(6): 771-785 and including supplemental information (2012).
Nelson et al., "Transient inactivation of Notch signaling synchronizes differentiation of neural progenitor cells," *Developmental Biology*, 304(2): 479-498 (2007).
Ng et al., "Forced Aggregation of Defined Numbers of Human Embryonic Stem Cells into Embryoid Bodies Fosters Robust, Reproducible Hematopoietic Differentiation," *Blood*, 106(5): 1601-1603 (Sep. 1, 2005).
Ng et al., "A protocol describing the use of a recombinant protein-based, animal product-free medium (APEL) for human embryonic stem cell differentiation as spin embryoid bodies," *Nature Protocols*, 3(5): 768-776 (Apr. 10, 2008).
Nicholas et al., "Functional maturation of hPSC-derived-forebrain interneurons requires an extended timeline and mimics human neural development," *Cell Stem Cell*, 12(5): 573-586 (2013).
Osakada et al., "Toward the generation of rod and cone photoreceptors from mouse, monkey and human embryonic stem cells," *Nature Biotechnology*, 26(2): 215-224 (Feb. 1, 2008).
Ozone et al., "Functional anterior pituitary generated in self-organizing culture of human embryonic stem cells," *Nat. Commun.*, 7: 10351 (2016).
Petros et al., "Pluripotent stem cells for the study of CNS development," *Frontiers in Molecular Neuroscience*, 4: Article 30 (Oct. 12, 2011).
Polejaeva et al., "Stem cell potency and the ability to contribute to chimeric organisms," *Reproduction*, 145(3): R81-R88 (2013).
RIKEN Press Release, "ES saibo kara Shishokabu Neuron Bunka Yudo to Hormon Sansei ni Seiko—Naibunpitsu ya Sesshoku Shogai no Kenkyu ni Koken suru Atarashii Tool" (Aug. 5, 2008).
Sakaguchi et al., "Generation of functional hippocampal neurons from self-organizing human embryonic stem cell-derived dorsomedial telencephalic tissue," *Nature Communications*, 6: 8896 (2015).
Schulz et al., "Differentiation of Human Embryonic Stem Cells to Dopaminergic Neurons in Serum-Free Suspension Culture," *Stem Cells*, 22(7): 1218-1238 (Jan. 1, 2004).
Shen et al., "The timing of cortical neurogenesis is encoded within lineages of individual progenitor cells," *Nat. Neurosci.*, 9(6): 743-751 (2006).
Sigma-Aldrich, "Laminin from mouse Engelbreth-Holm-Swarm (EHS) sarcoma," CAS No. 114956-81-9 Catalog Entry (Feb. 3, 2018).
Su et al., "Generation of cerebellar neuron precursors from embryonic stem cells," *Developmental Biology*, 290: 287-296 (2006).
Suga et al., "Self-formation of functional adenohypophysis in three-dimensional culture," *Nature*, 480(7375): 57-62 and Methods (2011).
Troy et al., "Commitment of Embryonic Stem Cells to an Epiderman Cell Fate and Differentiation in Vitro," *Dev. Dyn.*, 232(2): 293-300 (2005).
Watanabe et al., "A Rock inhibitor permits survival of dissociated human embryonic stem cells," *Nature Biotechnology*, 25(6): 681-686 (May 27, 2007).
Watanabe et al., "Directed differentiation of telencephalic precursors from embryonic stem cells," *Nature Neuroscience*, 8(3): 288-296 with supplementary figures 1-8 and descriptions therefor (Mar. 2005).
Wataya et al., "Minimization of exogenous signals in ES cell culture induces rostral hypothalamic differentiation," *Proc. Natl. Acad. Sci. USA.*, 105(33): 11796-11801 (Aug. 19, 2008).
Yang et al., "In Vitro Isolation and Expansion of Human Retinal Progenitor Cells," *Exp. Neurol.*, 177(1): 326-331 (2002).
Zhong et al., "In vitro culture and differentiation of fetal human retinal progenitor cells," *Journal of Clinical Rehabilitative Tissue Engineering Research*, 12(51): 10117-101120 (2008).
European Patent Office, Supplementary European Search Report in European Application No. 09758437 (Jun. 11, 2012).
Japanese Patent Office, International Search Report in International Patent Application No. PCT/JP2009/060396 (Aug. 4, 2009).

(56) References Cited

OTHER PUBLICATIONS

Japanese Patent Office, International Search Report in International Patent Application No. PCT/JP2010/070163 (Feb. 15, 2011).
International Bureau of WIPO, International Preliminary Report on Patentability in International Patent Application No. PCT/JP2009/060396 (Jan. 11, 2011).
Japanese Patent Office, Written Opinion of the International Searching Authority in International Patent Application No. PCT/JP2010/070163 (Feb. 15, 2011).

* cited by examiner

METHOD FOR DIFFERENTIATION INDUCTION IN CULTURED STEM CELLS

CROSS-REFERENCE TO RELATED APPLICATIONS

This patent application is a continuation of copending U.S. patent application Ser. No. 13/508,303, filed on Oct. 22, 2012, which is the U.S. national phase of International Patent Application PCT/JP2010/070163, filed Nov. 5, 2010, which claims the benefit of U.S. Provisional Patent Application No. 61/258,439, filed Nov. 5, 2009, which are incorporated by reference in their entireties herein.

TECHNICAL FIELD

The present invention relates to a method of differentiation induction of stem cells, more specifically to a method of differentiation induction of stem cells comprising combining quick re-aggregation and three-dimensional suspension culture in performing stem cell aggregate culture.

BACKGROUND ART

To date, some culturing methods for differentiation induction of nerves from pluripotent stem cells such as ES cells have been known, including those reported by the present inventors [Watanabe, K., Ueno, M., Kamiya, D., Nishiyama, A., Matsumura, M., Wataya, T., Takahashi, J. B., Nishikawa, S., Nishikawa, S.-i., Muguruma, K. and Sasai, Y. (2007), A ROCK inhibitor permits survival of dissociated human embryonic stem cells. Nature Biotechnology 25, 681-686, Su, H.-L.; Muguruma, K., Kengaku, M., Matsuo-Takasaki, M., Watanabe, K., and Sasai, Y. (2006), Generation of Cerebellar Neuron Precursors from Embryonic Stem Cells. Developmental Biology 290, 287-296; Ikeda, H., Watanabe, K., Mizuseki, K., Haraguchi, T., Miyoshi, H., Kamiya, D., Honda, Y., Sasai, N., Yoshimura, N., Takahashi, M. and Sasai, Y. (2005), Generation of Rx+/Pax6+ neural retinal precursors from embryonic stem cells. Proc. Natl. Acad. Sci. USA 102, 11331-11336; pamphlet for WO2005/123902; and JP-A-2008-99662]. There are high expectations for ES cell-derived nerve cells (e.g., dopamine nerve cells and the like) as a source of graft cells for cell transplantation therapy in regenerative medicine for intractable neurologic diseases. To this end, disease-related nerve cells that are present in the brain and surrounding tissues must be produced accurately. However, because an extremely large number of kinds of nerve cells are present in the brain and surrounding tissues, there are still many types of nerve cells and tissues for which efficient in vitro differentiation has been unsuccessful.

The retina, a component of the eyeball, derived from the diencephalon, occurs as a thin membranous tissue covering the inner wall behind the eyeball. Observed in the retina is a laminar structure of regularly arranged nerve cells. Nerve cells of the retina can be roughly divided into five types: photoreceptor cells (cones, rods), bipolar cells, horizontal cells, amacrine cells, and ganglion cells. Light is converted to an electric signal in photoreceptor cells; the signal (information) is transmitted to bipolar cells and horizontal cells via chemical synapses. Bipolar cells connect with amacrine cells and nerve ganglion cells via synapses, and the axons of ganglion cells, as optic nerves, communicate with the visual center of the cerebrum. For the treatment of retinopathies, etiologic research, drug discovery research, cell transplantation therapy research and the like have been conducted so far, but it is extremely difficult to obtain human retinal tissue for the sake of such research. Although it has recently become possible to induce the differentiation from induced pluripotent stem cells to retinal pigment epithelium [see Hirami Y, Osakada F, Takahashi K, Okita K, Yamanaka S, Ikeda H, Yoshimura N, Takahashi M. (2009), Generation of retinal cells from mouse and human induced pluripotent stem cells. Neurosci Lett. 458(3):126-31], it has been difficult to control the selective differentiation induction and genesis into particular retinal neurons and a retinal tissue containing the same.

The present inventors showed that dispersion suspension culture using a serum-free medium (the SFEB method) is effective as a method for differentiation induction of nerves from pluripotent stem cells such as animal and human ES cells [see Ikeda, H., Watanabe, K., Mizuseki, K., Haraguchi, T., Miyoshi, H., Kamiya, D., Honda, Y., Sasai, N., Yoshimura, N., Takahashi, M. and Sasai, Y. (2005), Generation of Rx+/Pax6+ neural retinal precursors from embryonic stem cells. Proc. Natl. Acad. Sci. USA 102, 11331-11336; Watanabe, K., Kamiya, D., Nishiyama, A., Katayama, T., Nozaki, S., Kawasaki, H., Mizuseki, K., Watanabe, Y., and Sasai, Y. (2005), Directed differentiation of telencephalic precursors from embryonic stem cells. Nature Neurosci. 8, 288-296; and pamphlet for WO2005/123902]. This method enables efficient differentiation induction of nerve cells and sensory cells of the forebrain, particularly of the cerebrum and the neural retina. The present inventors also succeeded in differentiation induction of brainstem tissues such as the cerebellum by adding a growth factor such as Wnt to the medium while performing the SFEB method.

However, an analytical study with mouse embryonic stem cells revealed that when the SFEB method was applied, about 30% of the cells differentiated into cerebral nerve cells, but the remaining majority occurred as a mixture of other kinds of nerve cells. Additionally, cerebral cortex cells accounted for only about 40% of the differentiation induction of cerebral nerve cells; the induction efficiency was not so high. Furthermore, most of the cerebral tissue induced by a conventional method such as the SFEB method failed to have a clear morphology of cortical tissue, only forming a disarrayed cell mass. Additionally, the conventional SFEB method does not enable efficient differentiation induction of diencephalon tissue, which develops on the most rostral side of the central nervous system.

CITATION LIST

Patent Literature patent document 1: WO2005/123902
patent document 2: JP-A-2008-99662

Non Patent Literature non-patent document 1: Watanabe, K., Ueno, M., Kamiya, D., Nishiyama, A., Matsumura, M., Wataya, T., Takahashi, J. B., Nishikawa, S., Nishikawa, S.-i., Muguruma, K. and Sasai, Y. (2007) A ROCK inhibitor permits survival of dissociated human embryonic stem cells. Nature Biotechnology 25, 681-686
non-patent document 2: Su, H.-L., Muguruma, K., Kengaku, M., Matsuo-Takasaki, M., Watanabe, K., and Sasai, Y. (2006) Generation of Cerebellar Neuron Precursors from Embryonic Stem Cells. Developmental Biology 290, 287-296 non-patent document 3: Ikeda, H., Watanabe, K., Mizuseki, K., Haraguchi, T., Miyoshi, H., Kamiya, D., Honda, Y., Sasai, N., Yoshimura, N., Takahashi, M. and Sasai, Y. (2005) Generation of Rx+/Pax6+ neural retinal precursors from embryonic stem cells. Proc. Natl. Acad. Sci. USA 102, 11331-11336 non-patent document 4: Hirami Y, Osakada F, Takahashi K, Okita K, Yamanaka S, Ikeda H, Yoshimura N, Takahashi M. (2009) Generation of retinal cells from mouse and human induced pluripotent stem cells. Neurosci Lett. 458(3): 126-31 non-patent document 5: Watanabe, K., Kamiya, D., Nishiyama, A., Katayama, T., Nozaki, S., Kawasaki, H., Mizuseki, K., Watanabe, Y., and Sasai, Y. (2005) Directed differentiation of telencephalic precursors from embryonic stem cells. Nature Neurosci. 8, 288-296

DISCLOSURE OF THE INVENTION

Problems to be Solved by the Invention

It is an object of the present invention to develop a highly practical method that enables differentiation induction of stem cells such as ES cells, particularly selective differentiation induction to cells that form retinal tissue.

Means of Solving the Problems

To explain the low efficiency of differentiation induction of nerve cells by the SFEB method, the present inventors hypothesized that the formation of an epithelial structure known as nerve epithelium between nerve progenitor cells in nerve tissue is necessary for their efficient differentiation, proliferation and histologic genesis into various nerve cells, including retinal cells, so that the stable formation of the epithelial structure is essential to efficient in vitro production of nerve cells and central nervous system tissues containing the same require. Based on this hypothesis, the present inventors extensively investigated differentiation induction of embryonic stem cells in the absence of serum, and found that by forming homogenous aggregates of stem cells in a serum-free medium, and suspension-culturing the aggregates in the presence of a basement membrane reference standard, nerve cells, particularly retinal progenitor cells, can be differentiation-induced from ES cells with high efficiency.

Later, the present inventors found that the retinal progenitor cells form an optic cup-like structure, and that by culturing them in an organ culture broth, a retinal tissue having a functional laminar structure comparable to the retinal structure after birth can be produced in vitro.

The present inventors conducted further investigations based on these findings, and have developed the present invention. Accordingly, the present invention provides:

[1] a method of differentiation induction of a stem cell into a nerve progenitor cell, comprising:
the step (1) of forming homogenous aggregates of stem cells in a serum-free medium; and
the step (2) of suspension-culturing the homogenous aggregates of stem cells in the presence of a basement membrane reference standard;
[2] the method according to [1], wherein the nerve progenitor cell is a retinal progenitor cell;
[3] the method according to [2], wherein the basement membrane reference standard contains an extracellular matrix molecule selected from among laminin, type IV collagen, heparan sulfate proteoglycan and entactin;
[4] the method according to [2] or [3], wherein the suspension culture is performed in the presence of KSR;
[5] the method according to [4], which is performed in the further presence of Nodal or Activin;
[6] a method of morphologically separating or identifying a mass of retinal progenitor cells, comprising:
the step (1) of forming homogenous aggregates of stem cells in a serum-free medium;
the step (2') of suspension-culturing the homogenous aggregates of stem cells in the presence of a basement membrane reference standard to allow an optic cup-like tissue to be self-formed in the aggregate;
[7] the method according to [6], wherein the basement membrane reference standard contains an extracellular matrix molecule selected from among laminin, type IV collagen, heparan sulfate proteoglycan and entactin;
[8] the method according to [6] or [7], wherein the suspension culture is performed in the presence of KSR;
[9] the method according to [8], which is performed in the further presence of Nodal or Activin;
[10] a method of differentiation induction of a retinal layer-specific neuron, comprising:
the step (1) of forming homogenous aggregates of stem cells in a serum-free medium;
the step (2') of suspension-culturing the homogenous aggregates of stem cells in the presence of a basement membrane reference standard to allow an optic cup-like tissue to be self-formed in the aggregate; and
the step (3) of suspension-culturing the self-formed optic cup-like tissue in an organ culture broth;
[11] the method according to [10], wherein the retinal layer-specific neuron is selected from among photoreceptor cells, horizontal cells, bipolar cells, amacrine cells and ganglion cells;
[12] the method according to [10] or [11], wherein the basement membrane reference standard contains an extracellular matrix molecule selected from among laminin, type IV collagen, heparan sulfate proteoglycan and entactin;
[13] the method according to any one of [10] to [12], wherein the suspension culture is performed in the presence of KSR;
[14] the method according to [13], which is performed in the further presence of Nodal or Activin;
[15] a method of producing a retinal tissue in vitro, comprising:
the step (1) of forming homogenous aggregates of stem cells in a serum-free medium;
the step (2') of suspension-culturing the homogenous aggregates of stem cells in the presence of a basement membrane reference standard to allow an optic cup-like tissue to be self-formed in the aggregate; and
the step (3) of suspension-culturing the self-formed optic cup-like tissue in an organ culture broth;
[16] the method according to [15], wherein the basement membrane reference standard contains an extracellular matrix molecule selected from among laminin, type IV collagen, heparan sulfate proteoglycan and entactin;
[17] the method according to [15] or [16], wherein the suspension culture is performed in the presence of KSR;
[18] the method according to [17], which is performed in the further presence of Nodal or Activin;
[19] a method of producing a retinal layer-specific neuron, comprising:
the step (1) of forming homogenous aggregates of stem cells in a serum-free medium;
the step (2') of suspension-culturing the homogenous aggregates of stem cells in the presence of a basement membrane reference standard to allow an optic cup-like tissue to be self-formed in the aggregate; and the step (3) of suspension-culturing the self-formed optic cup-like tissue in an organ culture broth;

[20] the method according to [19], wherein the retinal layer-specific neuron is selected from among photoreceptor cells, horizontal cells, bipolar cells, amacrine cells and retinal ganglion cells;

[21] the method according to [19] or [20], wherein the basement membrane reference standard contains an extracellular matrix molecule selected from among laminin, type IV collagen, heparan sulfate proteoglycan and entactin;

[22] the method according to any one of [19] to [21], wherein the suspension culture is performed in the presence of KSR;

[23] the method according to [22], which is performed in the further presence of Nodal or Activin;

[24] a culture product produced by the method according to any one of [1] to [23];

[25] a screening method for a test substance, comprising using the culture product according to [24];

[26] a toxicity study method for a test substance, comprising using the culture product according to [24];

[27] a retina for transplantation containing the culture product according to [24].

Effect of the Invention

According to the present invention, it is possible to induce the differentiation of a stem cell into a nerve progenitor cell, particularly into a retinal progenitor cell, efficiently. The method of the present invention also enables efficient differentiation induction into nervous system cells, particularly into retinal cells, a task that has been difficult to achieve by the conventional method of differentiation induction. Therefore, the method of the present invention is particularly useful in applying cytotherapy for diseases associated with abnormalities in a nerve tissue, particularly in retinal tissue.

According to the method of the present invention, it is also possible to selectively inducing the differentiation of retinal layer-specific neurons. The retinal tissue obtained by the method of the present invention has a laminar structure that is extremely similar to the living retina. Furthermore, the three-dimensional laminar structure of this retinal tissue has formed a functional nerve network that is highly similar to the living retina. Therefore, the method of the present invention is also highly useful in providing "tissue materials" for use in regenerative medicine for nerve tissues, particularly for retinal tissue, and in providing "tissue materials" that serve well in drug discovery seeds screening or toxicity tests of pharmaceuticals, reagents and the like that act on the retina, and the like, in the production of pharmaceuticals for nerve tissue disorders, particularly for retinal tissue disorders.

The present invention is also useful in that differentiation of stem cells can be induced without using an animal-derived cell as an inductor, so that the risk levels in the transplantation of cells obtained by stem cell culture can be reduced to that in allotransplantation.

BEST MODE FOR CARRYING OUT THE INVENTION

Figure 1A:
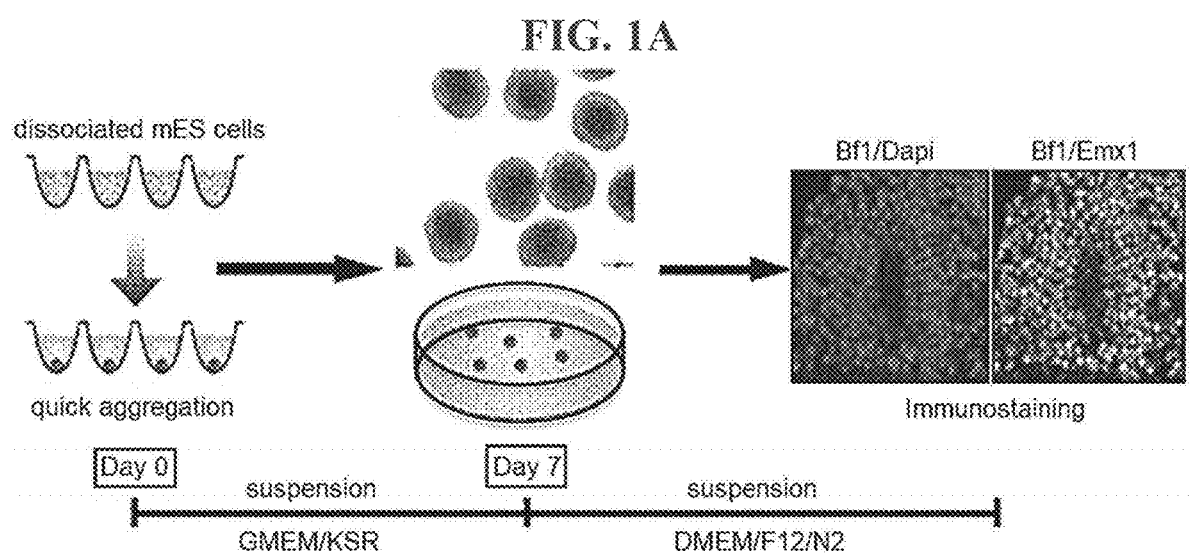
FIG. 1A illustrates the steps of the sFEBq method.
Figure 1B:
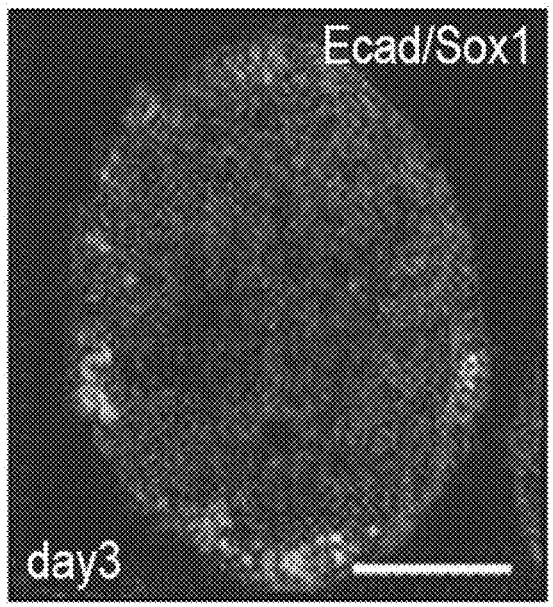
FIGS. 1B-1O show that aggregates of mouse ES cells obtained by the SFEBq method differentiate into homogenous nerve cells having an epithelium-like structure.
Figure 1C:
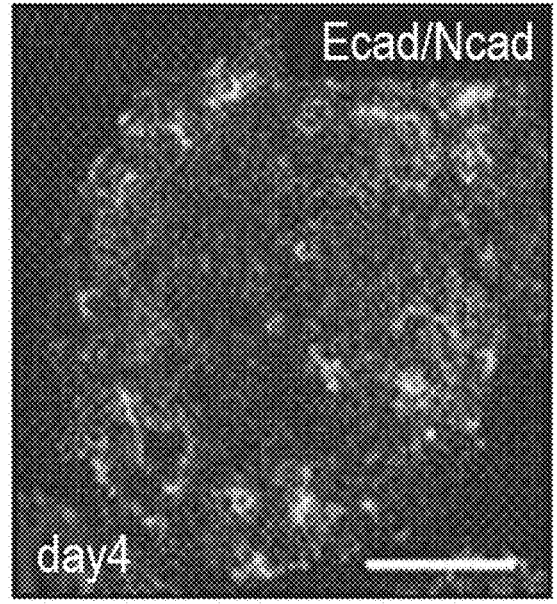
Figure 1D:
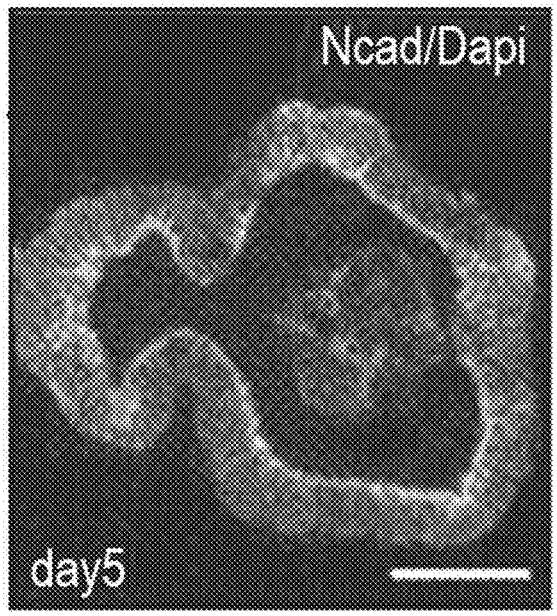
Figure 1E:
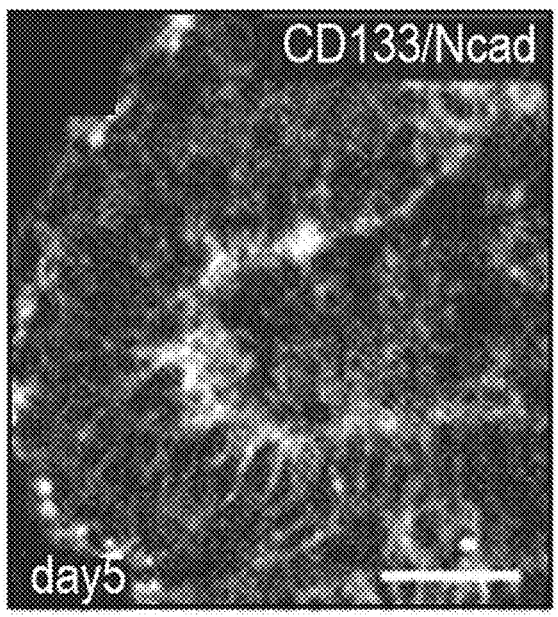
Figure 1F:
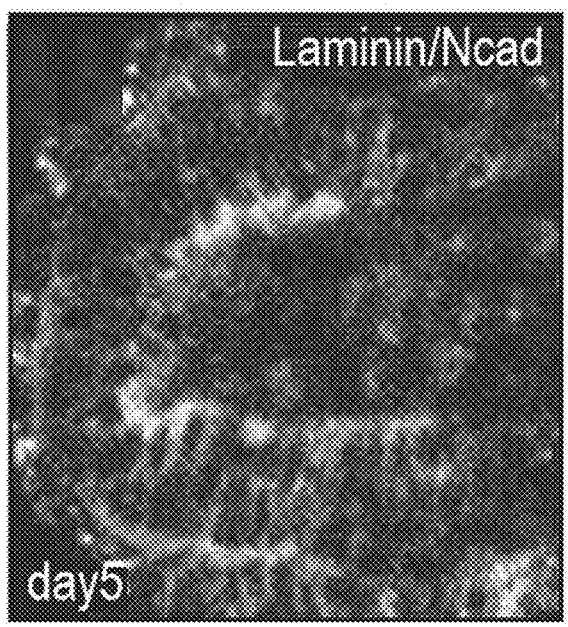
Figure 1G:
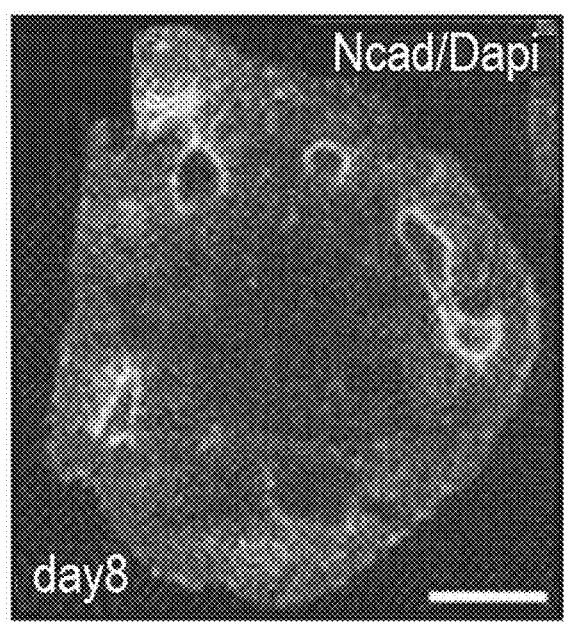

The present invention is hereinafter described in detail.

(1) Stem Cells

"A stem cell" refers to a cell capable of retaining a constant potential for differentiation even after cell division. Examples of stem cells include embryonic stem cells (ES cells) with pluripotency derived from a fertilized egg or clone embryo, somatic stem cells and pluripotent stem cells that are present in tissues in a living organism, hepatic stem cells, dermal stem cells, and reproductive stem cells that serve as the bases for respective tissues, pluripotent stem cells derived from a reproductive stem cells, pluripotent stem cells obtained by nuclear reprogrammed somatic cells, and the like.

In particular, "a pluripotent stem cell" refers to a stem cell permitting in vitro culture, and having the potential for differentiating into all cells, but the placenta, constituting the body [tissues derived from the three primary germ layers of the embryo (ectoderm, mesoderm, endoderm)] (pluripotency); embryonic stem cells are also included. "A pluripotent stem cell" is obtained from a fertilized egg, clone embryo, reproductive stem cell, or stem cell in tissue. Also included are cells having differentiation pluripotency similar to that of embryonic stem cells, conferred artificially by transferring several different genes to a somatic cell (also referred to as induced pluripotent stem cells). Pluripotent stem cells can be prepared by a method known per se. Available methods include, for example, methods described in Cell 131(5), pp. 861-872, Cell 126(4), pp. 663-676 and elsewhere.

As stem cells, cells derived from a warm-blooded animal, for example, preferably from a mammal, can be used. Mammals include, for example, laboratory animals, including rodents such as mice, rats, hamsters and guinea pigs, and rabbits; domestic animals such as pigs, cattle, goat, horses, and sheep; companion animals such as dogs and cats; primates such as humans, monkeys, orangutans, and chimpanzees.

Examples of stem cells useful in the method of the present invention include embryonic stem cells of a mammal or the like established by culturing a pre-implantation early embryo (hereinafter, abbreviated as "embryonic stem cells I"), embryonic stem cells established by culturing an early embryo prepared by nuclear-transplanting the nucleus of a somatic cell (hereinafter, abbreviated as "embryonic stem cells II"), induced pluripotent stem cells (iPS cells) established by transferring several different transcriptional factors to a somatic cell, and pluripotent stem cells prepared by modifying a gene on a chromosome of embryonic stem cells I, embryonic stem cells II or iPS cells using a gene engineering technique (hereinafter, abbreviated as "modified pluripotent stem cells").

More specifically, embryonic stem cells I include embryonic stem cells established from an inner cell mass that constitutes an early embryo, EG cells established from a primordial germ cell, cells isolated from a cell population possessing the pluripotency of pre-implantation early embryos (for example, primordial ectoderm), and cells obtained by culturing these cells.

Embryonic stem cells I can be prepared by culturing a pre-implantation early embryo according to a method described in the literature (Manipulating the Mouse Embryo A Laboratory Manual, Second Edition, Cold Spring Harbor Laboratory Press (1994)).

Embryonic stem cells II can be prepared using methods reported by Wilmut et al. [Nature, 385, 810 (1997)], Cibelli et al. [Science, 280, 1256 (1998)], Akira Iritani et al. [Protein, Nucleic Acid and Enzyme, 44, 892 (1999)], Baguisi et al. [Nature Biotechnology, 17, 456 (1999)], Wakayama et al. [Nature, 394, 369 (1998); Nature Genetics, 22, 127 (1999); Proc. Natl. Acad. Sci. USA, 96, 14984 (1999)], Rideout III et al. [Nature Genetics, 24, 109 (2000)] and others, for example, as described below.

By extracting the nucleus of a mammalian cell and then reprogramming the nucleus (an operation to return the nucleus to a state to resume development), initiating development using a method involving injection into an enucleated unfertilized egg of a mammal, and culturing the egg that has started development, an egg that has the nucleus of another somatic cell, and has begun normal development, is obtained.

A plurality of methods of reprogramming the nucleus of a somatic cell are known. For example, the nucleus can be reprogrammed by changing the medium used to culture the nucleus donor cell from a medium containing 5 to 30%, (preferably 10%) of fetal calf serum (e.g., M2 medium) to an oligotrophic medium containing 0 to 1% (preferably 0.5%) of fetal calf serum, and culturing the cell for 3 to 10 days (preferably 5 days) to induce the cell cycle into a resting phase state (G0 stage or G1 stage).

The nucleus can also be reprogrammed by injecting the nucleus of the nucleus donor cell into an enucleated unfertilized egg of a mammal of the same species, and culturing the cell for several hours, preferably for about 1 to 6 hours.

The reprogrammed nucleus is able to begin development in the enucleated unfertilized egg. A plurality of methods of allowing the reprogrammed nucleus to begin development in the enucleated unfertilized egg are known. By transplanting a nucleus reprogrammed by inducing the cell cycle to a resting phase state (phase G0 or phase G1) into an enucleated unfertilized egg of a mammal of the same species by the electrofusion method and the like, the egg can be activated and allowed to begin development.

A nucleus reprogrammed by injecting the nucleus into an enucleated unfertilized egg of a mammal of the same species is transplanted back to an enucleated unfertilized egg of a mammal of the same species by a method using a micromanipulator or the like, and stimulated with an egg activator (e.g., strontium and the like), and thereafter treated with an inhibitor of cell division (e.g., cytochalasin B and the like) to suppress the release of the second polar body, whereby development can be initiated. This method is suitable when the mammal is, for example, a mouse or the like.

Provided that an egg that once began to develop is obtained, embryonic stem cells can be acquired using publicly known methods described in Manipulating the Mouse Embryo A Laboratory Manual, Second Edition, Cold Spring Harbor Laboratory Press (1994); Gene Targeting, A Practical Approach, IRL Press at Oxford University Press (1993); Biomanual Series 8 Gene Targeting, Preparation of Mutant Mice Using ES Cells, Yodosha (1995) and the like.

iPS cells can be produced by transferring Oct3/4, Sox2 and Klf4 (c-Myc or n-Myc further added as required) to somatic cells (e.g., fibroblasts, dermal cells and the like) (Cell, 126: p. 663-676, 2006; Nature, 448: p. 313-317, 2007; Nat Biotechnol, 26: p. 101-106, 2008; Cell 131: 861-872, 2007).

Modified pluripotent stem cells can be prepared by, for example, homologous recombination technology. Examples of the gene on the chromosome to be modified in preparing modified pluripotent stem cells, histocompatibility antigen genes, genes related to diseases based on neural cell disorders, and the like. A modification of the target gene on the chromosome can be performed using methods described in Manipulating the Mouse Embryo A Laboratory Manual, Second Edition, Cold Spring Harbor Laboratory Press (1994); Gene Targeting, A Practical Approach, IRL Press at Oxford University Press (1993); Biomanual Series 8 Gene Targeting, Preparation of Mutant Mice Using ES Cells, Yodosha (1995) and the like.

Specifically, for example, a genomic gene of a target gene to be modified (for example, histocompatibility antigen genes, disease-related genes and the like) is isolated, and a target vector for homologous recombination of the target gene is prepared using the genomic gene isolated. By transferring the target vector prepared to an embryonic stem cell, and selecting cells undergoing homologous recombination between the target gene and the target vector, stem cells having a modified gene on the chromosome can be prepared.

Methods of isolating a genomic gene of a target gene include publicly known methods described in Molecular Cloning, A Laboratory Manual, Second Edition, Cold Spring Harbor Laboratory Press (1989), Current Protocols in Molecular Biology, John Wiley & Sons (1987-1997) and elsewhere. A genomic gene of a target gene can also be isolated by using a genomic DNA library screening system (produced by Genome Systems), Universal GenomeWalker™ Kits (produced by CLONTECH) and the like.

Preparation of a target vector for homologous recombination of a target gene and efficient sorting of a homologous recombinant can be achieved by a method described in Gene Targeting, A Practical Approach, IRL Press at Oxford University Press (1993); Biomanual Series 8 Gene Targeting, Preparation of Mutant Mice Using ES Cells, Yodosha (1995) and elsewhere. The target vector used may be any one of the replacement type and the insertion type. Useful methods of sorting include positive selection, promoter selection, negative selection, poly A selection and the like.

Available methods of selecting a desired homologous recombinant from among the sorted cell lines include Southern hybridization, PCR and the like for genomic DNA.

Stem cells are available from specified organizations, and commercial products may be purchased. For example, the human embryonic stem cells KhES-1, KhES-2 and KhES-3 are available from the Institute for Frontier Medical Sciences, Kyoto University. Examples of mouse embryonic stem cells include EB5 cells and the like.

Stem cells can be cultured for maintenance by a method known per se. For example, stem cells can be maintained by cultivation without feeder cells with the addition of fetal calf serum (FCS), Knockout™ Serum Replacement (KSR), and LIF.

(2) Cells Permitting Differentiation Induction by the Method of the Present Invention According to the present invention, differentiated cells can be obtained from stem cells, preferably pluripotent stem cells such as embryonic stem cells. The cells differentiation-induced from a stem cell by the method of the present invention are preferably nervous system cells. The cells are more preferably nerve stem cells, particularly preferably nerve progenitor cells, most preferably retinal progenitor cells. Nerve cells obtained via nerve progenitor cells can also be obtained by the present invention. While the type of such nerve cells is not particularly limited, retinal cells are preferable. The cells obtained by the method of the present invention can be identified by a method known per se, for example, by the expression of a cell marker.

Examples of markers of nervous system cells include, but are not limited to, Rx, NCAM, TuJ1, tyrosine hydroxylase (TH), serotonin, nestin, MAP2, MAP2ab, NeuN, GABA, glutamates, ChAT, Sox1, Bf1, Emx1, VGluT1, Pax, Nkx, Gsh, Telencephalin, GluR1, CamKII, Ctip2, Tbr1, Reelin, Tbr1, Brn2 and the like. The expression of a marker gene is analyzed by, for example, performing quantitative PCR using the 7500 Fast Real-Time PCR System (Applied Biosystems) in accordance with the manufacturer's instructions, and normalizing the obtained data by the expression of GAPDH. The method of quantitative PCR is obvious to those skilled in the art. Alternatively, cells may be manipulated to allow the desired marker gene to be expressed as a fusion protein of a marker gene product and GFP or the like (knock-in). It is also possible to detect the expression of the protein using an antibody specific for a marker gene product. Hereinafter, to exemplify cells that can be differentiation-induced by the method of the present invention, nerve stem cells are described in detail.

A nerve stem cell refers to a cell having both the potential for differentiation into nerve cells, astrocytes and oligodendrocytes and the potential for autoreproduction, functioning in the brain to supply nerve cells, astrocytes and oligodendrocytes. The nerve stem cells that differentiate into nerve cells, in particular, are called nerve progenitor cells. In the present specification, nerve stem cells are understood to include nerve progenitor cells.

Available methods of confirming the identity of the cell obtained as a nerve stem cell include a method wherein the cell is actually transplanted to a living brain and its differentiating potential is confirmed, a method wherein the nerve stem cell is differentiation-induced to nerve cells/astrocytes/oligodendrocytes in vitro, and the like [Mol. Cell. Neuroscience, 8, 389(1997); Science, 283, 534(1999)]. Nerve stem cells having these functions are stainable with an anti-nestin antibody that recognizes cytoskeletal protein nestin, which is a marker whose expression has been confirmed in nerve progenitor cells, and an anti-Sox1 antibody that recognizes the nuclear factor Sox1 [Science, 276, 66(1997)]. Therefore, it is also possible to confirm the identity of the nerve stem cell by staining with an anti-nestin antibody or anti-Sox1 antibody. However, despite their identity as nerve progenitor cells, retinal progenitor cells are exceptionally not stainable with an anti-nestin antibody or anti-Sox1 antibody, but are instead stainable with anti-Rx and anti-Pax6 antibodies, which recognize Rx and Pax6, which are nuclear factors expressed in retinal progenitor cells. Therefore, retinal progenitor cells can be identified as cells that are positive for Rx and Pax6 and negative for nestin and Sox1 (Ikeda et al, PNAS 2005).

Nerve progenitor cells are not particularly limited, as far as they have the potential for differentiating into various nerve cells, and they include cerebral progenitor cells, cerebellar progenitor cells, midbrain progenitor cells, afterbrain progenitor cells, diencephalon progenitor cells, retinal progenitor cells and the like. In the present invention, preferred nerve progenitor cells are diencephalon progenitor cells and retinal progenitor cells, with greater preference given to retinal progenitor cells. The method of the present invention allows these optionally chosen nerve progenitor cells to be differentiation-induced; in particular, diencephalon progenitor cells and retinal progenitor cells, preferably retinal progenitor cells, can be differentiation-induced efficiently.

Alternatively, nerve progenitor cells, particularly retinal progenitor cells, obtained by the method of the present invention can be characterized by cell markers. Nerve progenitor cell markers include, but are not limited to, Rx, NCAM, Sox1, Bf1, nestin, Emx1, Pax6, Nkx2.1, and Gsh2. Retinal progenitor cell markers, in particular, include Rx, Pax6, Chx10 (with the provision of co-expression with Ki67) and the like.

Nerve cell markers include, but are not limited to, TuJ1, tyrosine hydroxylase (TH), serotonin, MAP2, MAP2ab, NeuN, GABA, glutamates, ChAT, VGluT1, GluR1, CamKII, Reelin, Telencephalin, Ctip2, Tbr1, Tbr2, Brn2, L7 and the like. The nerve progenitor cells obtained by the method of the present invention are Rx-positive at a high frequency of at least 60% or more, preferably 80% or more, more preferably about 80 to 90%.

According to the present invention, it is also possible to induce differentiation of stem cell into retinal cells via retinal progenitor cells. Particularly, the retinal cells obtained by differentiation induction by the present invention are obtained as a constituent of a cell aggregate having a three-dimensional laminar structure that is extremely similar to the living retina. Hence, the retinal cells of the present invention can assume a three-dimensional laminar structure that is morphologically extremely similar to the living retina, so that neurons specific for respective retinal layers (herein, these are described as "retinal layer-specific neurons" together) are included in the scope of the invention.

The retinal cells obtained by the present invention include, but are not limited to, all the cells that constitute the retina; cells constituting the individual retinal layers (retinal layer-specific neurons) include, for example, photoreceptor cells, horizontal cells, bipolar cells, amacrine cells, retinal ganglion cells and the like. According to the present invention, these cells can be efficiently obtained by differentiation induction from a stem cell. The type of the retinal cells obtained by the present invention can be identified by a method known per se, for example, by the expression of a cell marker.

Retinal cell markers include, but are not limited to, Rx (retinal progenitor cells), PAX6 (progenitor cells), nestin (expressed in hypothalamic neuron progenitor cells, but not in retinal progenitor cells), Sox1 (expressed in hypothalamic nerve epithelium, but not in the retina), Crx (photoreceptor cell progenitor cells) and the like. Particularly, markers of the above-described retinal layer-specific neurons include, but are not limited to, Chx10 (bipolar cells), L7 (bipolar cells), Tuj1 (ganglion cells), Brn3 (ganglion cells), calretinin (amacrine cells), calbindin (horizontal cells), rhodopsin (photoreceptor cells), recoverin (photoreceptor cells), RPE65 (pigment epithelial cells), Mitf (pigment epithelial cells) and the like.

(3) Method of Differentiation Induction of the Present Invention

The present invention provides a method of differentiation induction of a stem cell into nerve progenitor cells, comprising the step of forming homogenous aggregates of stem cells in a serum-free medium and the step of suspension-culturing the homogenous aggregates of stem cells in the presence of a basement membrane reference standard.

(3-1) The Step of Forming Homogenous Aggregates of Stem Cells in a Serum-Free Medium [Step (1)]

"Forming homogenous aggregates of stem cells" refers to forming qualitatively homogenous aggregates of stem cells by allowing "a given number of dispersed stem cells to aggregate quickly" in allowing stem cells to assemble and form aggregates of stem cells and culturing the aggregates (aggregate culture), referring particularly to promoting the epithelization of cells deriving from stem cells by allowing "the cells to aggregate quickly". Hence, as used herein, the term "to allow the cells to aggregate quickly" refers to forming with high reproducibility an epithelium-like structure in the cells produced by allowing stem cells to aggregate homogenously.

Any method may be employed to form homogenous aggregates of stem cells, as far as homogenous aggregates of stem cells are formed by allowing "the cells to aggregate quickly", and an epithelium-like structure of the cells produced from the stem cells is formed with high reproducibility. Such methods include, for example, a method wherein cells are enclosed in small spaces using a plate with small wells (96-well plate), micropores or the like, a method wherein cells are aggregated by centrifugation for a short time using small centrifugal tubes, and the like.

Any incubator can be used to form aggregates, as far as it allows homogenous aggregates of stem cells to be formed by allowing "the cells to aggregate quickly"; those skilled in the art are able to determine the choice as appropriate. Such incubators include, for example, flasks, tissue culture flasks, dishes, Petri dishes, tissue culture dishes, multi-dishes, microplates, micro-well plates, micropores, multi-plates, multi-well plates, chamber slides, Petri dishes, tubes, trays, culturing bags, and roller bottles. From the viewpoint of forming homogenous aggregates, it is preferable that these incubators be non-cell-adhesive. Useful non-cell-adhesive incubators include incubators whose surfaces have not undergone an artificial treatment (e.g., coating with extracellular matrix and the like) for improving the cell adhesiveness.

A medium used to form aggregates can be prepared using a medium in use for animal cell culture as a basal medium. Any basal medium available for culturing animal cells can be used; examples include, but are not limited to, BME medium, BGJb medium, CMRL 1066 medium, Glasgow MEM medium, Improved MEM Zinc Option medium, IMDM medium, Medium 199 medium, Eagle's MEM medium, αMEM medium, DMEM medium, Ham's medium, RPMI 1640 medium, Fischer's medium, a mixed medium thereof and the like.

Here, a serum-free medium used to form aggregates means a medium not containing an unadjusted or unpurified serum. Any such serum-free medium can be used in the present invention. However, to avoid the painstakingness in preparing the serum-free medium, a serum-free medium (GMEM or dMEM, 0.1 mM 2-mercaptoethanol, 0.1 mM non-essential amino acids Mix, 1 mM sodium pyruvate) supplemented with an appropriate amount (e.g., 1-20%) of commercially available KSR can be used.

The serum-free medium may contain a serum substitute. The serum substitute can be, for example, one containing as appropriate albumin, transferrin, fatty acids, collagen precursor, trace elements, 2-mercaptoethanol or 3'-thiolglycerol, or equivalents thereof and the like. These serum substitutes can be prepared by, for example, a method described in WO98/30679. Also, to carry out the method of the present invention more conveniently, a commercially available serum substitute can be utilized. Examples of such commercially available serum substitutes include Chemically-defined Lipid Concentrated (produced by Gibco Company) and Glutamax (produced by Gibco Company).

The serum-free medium used for the suspension culture can also contain fatty acids or lipids, amino acids (e.g., non-essential amino acids), vitamins, growth factors, cytokines, antioxidants, 2-mercaptoethanol, pyruvic acid, buffering agents, inorganic salts and the like.

The concentration of stem cells at the time of aggregate formation can be set as appropriate by those skilled in the art, such that aggregates of stem cells will be formed more homogenously and efficiently. The concentration of stem cells at the time of aggregate formation may be any concentration that allows homogenous aggregates of stem cells to be formed. In case of differentiation culture of mouse ES cells using a 96-well microwell plate, for example, their suspensions prepared to obtain a cell density of about $1 \times 10^3$ to about $5 \times 10^3$ cells, preferably about $2 \times 10^3$ to about $4 \times 10^3$ cells, per well, are added to the plate, and the plate is kept to stand to allow aggregates to be formed. In case of human ES cells, suspensions prepared to obtain a cell density of about $1 \times 10^3$ to about $12 \times 10^3$ cells, preferably about $4 \times 10^3$ to about $10 \times 10^3$ cells, per well, are used.

Other culturing conditions such as culturing temperature and $CO_2$ concentration at the time of aggregate formation can be set as appropriate. The culturing temperature is not particularly limited, and is, for example, about 30 to 40° C., preferably about 37° C. The $CO_2$ concentration is, for example, about 1 to 10%, preferably about 5%.

Although the time to the formation of aggregates can be determined as appropriate according to the choice of stem cell used, as far as cells are allowed to aggregate quickly, it is desirable that the formation be performed as soon as possible to ensure the formation of homogenous aggregates. Conventionally, this formation of aggregates is performed over about 2 days (see, for example, Watanabe, K. et al., Nature Neurosci. 8, 288-296, Schuldiner M, Benvenisty N. Factors controlling human embryonic stem cell differentiation. Methods Enzymol. 2003; 365: 446-461). In the present invention, by contrast, this time is shortened to enable efficient differentiation induction of desired nerve cells and the like. In case of mouse embryonic stem cells, for example, it is desirable that aggregates be formed preferably within 12 hours, more preferably within 6 hours. Meanwhile, in case of human embryonic stem cells, it is desirable that aggregates be formed preferably within 24 hours, more preferably within 12 hours. If this time is exceeded, homogenous aggregates of stem cells cannot be formed, which in turn can cause a remarkable reduction in differentiation efficiency in the subsequent step. This time to aggregate formation can be adjusted as appropriate by choosing a tool for cell aggregation, centrifugal conditions and the like by those skilled in the art.

Those skilled in the art are able to make a judgement concerning the "homogenous" formation of aggregates of stem cells and the formation of an epithelium-like structure in each cell type that forms aggregates, on the basis of the size of the aggregate masses and the number of cells therein, macroscopic morphology, microscopic morphology as analyzed by histological staining and uniformity thereof, the expression of differentiation and non-differentiation markers and uniformity thereof, the control of the expression of differentiation markers and synchronicity thereof, inter-aggregate reproducibility of differentiation efficiency, and the like.

Specifically, homogenous aggregates of stem cells can be formed by, for example, a method wherein embryonic stem cells are cultured for maintenance, followed by dispersion treatment, and suspended in an appropriate medium (e.g., Glasgow MEM medium supplemented with 10% KSR, 0.1 mM non-essential amino acid solution, 2 mM glutamine, 1 mM pyruvic acid and 0.1 mM 2-mercaptoethanol; may contain appropriate amounts of factors described below, added as required, and the like), and the cells are suspended in 150 μL of the above-described medium at $3 \times 10^3$ cells per well using a non-cell-adhesive U-bottom 96-well culture plate to form aggregates rapidly.

(3-2) The Step of Suspension-Culturing the Homogenous Aggregates of Stem Cells in a Serum-Free Medium in the Presence of a Basement Membrane Reference Standard [Step (2)]

This is a step wherein the homogenous aggregates of stem cells formed in the step (1) are subjected to suspension culture in the presence of a basement membrane reference standard to induce the differentiation of stem cells.

"The basement membrane reference standard" may be any one that contains a basement membrane constituent component having the function of controlling the morphology, differentiation, proliferation, motor, functional expression and the like of epithelial cell-like cells when desired cells capable of forming a basement membrane are seeded and cultured thereon. Such a basement membrane reference standard can be prepared by, for example, removing the cells capable of forming the basement membrane, adhering to a support via the basement membrane, using a solution capable of dissolving the lipids of the cells, an alkali solution and the like.

Preferred basement membrane reference standards include commercially available products as basement membrane components (e.g., Matrigel) and those containing an extracellular matrix molecule publicly known as a basement membrane component (e.g., laminin, type IV collagen, heparan sulfate proteoglycan, entactin and the like). These extracellular matrix molecules to be used are desirably purified products.

As such extracellular matrix molecules, laminin and entactin can be preferably used. Particularly, when Nodal and Activin to be mentioned later are concurrently used for performing the present invention, purified laminin and entactin can be preferably used as basement membrane components.

Matrigel is a basement membrane preparation derived from Engelbreth Holm Swarn (EHS) mouse sarcoma. The major components of Matrigel are type IV collagen, laminin, heparan sulfate proteoglycan, and entactin. In addition, TGF-β, fibroblast growth factor (FGF), tissue plasminogen activator, and the growth factor naturally produced by EHS tumors are also contained. "Growth factor reduced products" of Matrigel have lower concentrations of growth factors than in ordinary Matrigel; the standard concentrations thereof are <0.5 ng/ml for EGF, <0.2 ng/ml for NGF, <5 μg/ml for PDGF, 5 ng/ml for IGF-1, and 1.7 ng/ml for TGF-β. In the method of the present invention, it is preferable to use "a growth factor reduced product".

The concentration of the basement membrane reference standard added to the medium for suspension culture in this step is not particularly limited, as far as the epithelial structure of a nerve tissue (e.g., retinal tissue) is stably maintained. For example, purified laminin and entactin can be preferably used. Particularly, when Nodal and Activin to be mentioned later are used (laminin/entactin complex is used), it is generally added at a concentration of 1 μg/mL-5000 μg/mL, preferably 10 μg/mL-2000 μg/mL, more preferably 20 μg/mL-1000 μg/mL, and most preferably 50 μg/mL-500 μg/mL, to a medium. When using Martigel, for example, it is added preferably in a volume 1/100 to 1/20, more preferably in a volume 1/100 to 1/50, of the volume of the culture broth. Although the basement membrane reference standard may be added to the medium already at the start of culturing the stem cell, it is added to the medium preferably within several days after the start of suspension culture (e.g., 1 to 3 days after the start of suspension culture).

"To suspension-culture homogenous aggregates of stem cells" or "to culture homogenous aggregates of stem cells as suspended aggregates (also referred to as aggregate masses)" refers to culturing the population of stem cells having assembled to form homogenous aggregates, obtained in the above-described step (1), in a culture medium under conditions that are non-adhesive to the cell incubator (herein, the above-described steps (1) and (2) are sometimes described as "the modified SFEBq method" together; the method wherein no basement membrane reference standard is used in the step (2) is described as "the SFEBq method"). When stem cells are suspension-cultured, the culture is preferably performed in the absence of feeder cells to facilitate the formation of suspended aggregates, and/or to achieve efficient induction of differentiation (e.g., induction of differentiation into ectodermal cells such as nervous system cells).

A medium used in the suspension culture of the aggregates obtained in the above-mentioned step (1) can be prepared with a medium for animal cell culture as the basal medium. The basal medium is not particularly limited, as far as it is a medium that can be used for animal cell culture; for example, BME medium, BGJb medium, CMRL 1066 medium, Glasgow MEM medium, Improved MEM Zinc Option medium, IMDM medium, Medium 199 medium, Eagle MEM medium, αMEM medium, DMEM medium, Ham medium, RPMI 1640 medium, Fischer's medium, and a mixed medium thereof and the like can be mentioned. Unless otherwise specified, the medium used in the step (1) may be used as it is for the suspension culture.

When the above-mentioned aggregates are suspension-cultured, a serum-free medium is used as the medium. Here, a serum-free medium means a medium that does not contain unadjusted or unpurified serum. A medium containing a purified blood-derived component or animal tissue-derived component (for example, growth factor) is to be construed as a serum-free medium, as far as it does not contain unadjusted or unpurified serum.

The serum-free medium used in the suspension culture can be, for example, one containing a serum substitute. The serum substitute can, for example, be one containing as appropriate an albumin (for example, lipid-rich albumin), transferrin, fatty acids, insulin, collagen precursor, trace elements, 2-mercaptoethanol or 3'-thiolglycerol, or their equivalents and the like. Such serum substitutes can be prepared by, for example, a method described in WO98/30679. To facilitate easier implementation of a method of the present invention, commercially available serum substitutes can be utilized. Examples of such commercially available serum substitutes include Knockout Serum Replacement (KSR), Chemically-defined Lipid Concentrated (produced by Gibco) and Glutamax (produced by Gibco).

In addition, the serum-free medium used in the method of the present invention can contain fatty acids or lipids, amino acids (for example, non-essential amino acids), vitamins, growth factors, cytokines, anti-oxidants, 2-mercaptoethanol, pyruvic acid, buffering agents, inorganic salts and the like. For example, 2-mercaptoethanol can be used without particular limitations as far as it is used at a concentration suitable for stem cell culture, and it can be used at concentrations of, for example, about 0.05 to 1.0 mM, preferably about 0.1 to 0.5 mM, more preferably about 0.2 mM.

The serum-free medium used for the suspension culture is not particularly limited, as far as it is as described above. However, from the viewpoint of avoiding the painstakingness in the preparation, and of efficiently inducing the differentiation of stem cells into nerve progenitor cells, preferably retinal progenitor cells, it is preferable that a serum-free medium (GMEM or dMEM, 0.1 mM 2-mercaptoethanol, 0.1 mM non-essential amino acids Mix, 1 mM sodium pyruvate) supplemented with an appropriate amount of commercially available KSR (Knockout Serum Replacement) be used as the serum-free medium. The amount of KSR added to the serum-free medium is not particularly limited. In case of mouse ES cells, for example, the amount added is normally 1 to 20% (v/v). When retinal progenitor cells are to be differentiation-induced from mouse ES cells more efficiently, the amount added is preferably 1 to 5%, most preferably 2%. In case of human ES cells, the amount of KSR added is normally 1 to 20%. When retinal progenitor cells are to be differentiation-induced from human ES cells more efficiently, the amount of KSR added is preferably 2 to 20%. By suspension-culturing the aggregates with the addition of KSR, in addition to the aforementioned basement membrane reference standard, the method of differentiation induction of the present invention described below and the like can be performed more efficiently.

The culture vessel used for the suspension culture is not particularly limited, as far as it allows suspension culture of cells; examples include flasks, tissue culture flasks, dishes, Petri dishes, tissue culture dishes, multi-dishes, microplates, micro-well plates, multi-plates, multi-well plates, chamber slides, Petri dishes, tubes, trays, culturing bags, and roller bottles.

When aggregates are suspension-cultured, the culture vessel is preferably non-adhesive to cells. As the non-adhesive-to-cell culture vessel, a culture vessel whose surface has not been artificially treated for the purpose of increasing the adhesiveness to cells (e.g., coating treatment with extracellular matrix and the like) can be used.

Other culturing conditions such as culturing temperature, $CO_2$ concentration and $O_2$ concentration at the time of aggregate suspension culture can be set as appropriate. The culturing temperature is not particularly limited, and is, for example, about 30 to 40° C., preferably about 37° C. The $CO_2$ concentration is, for example, about 1 to 10%, preferably about 5%. Meanwhile, when retinal progenitor cells are to be differentiation-induced, and taking into account the high oxygen demand thereby, the $O_2$ concentration is, for example, 20 to 70%, preferably 20 to 50%, more preferably 20 to 40%. The culturing time in this step is not particularly limited, and is normally 48 hours or more, preferably 7 days or more.

After suspension culture, the aggregates may be kept as they are or dispersion-treated (e.g., trypsin/EDTA treatment), and the cells may be further cultured under adhesive conditions (hereinafter, described as "adhesion culture" if required). If adhesion culture is performed, it is preferable that a cell-adhesive incubator, for example, an incubator coated with an extracellular matrix and the like (e.g., poly-D-lysine, laminin, entactin, fibronectin) be used. Culturing conditions such as culturing temperature, $CO_2$ concentration, $O_2$ concentration and culturing time in adhesion culture can easily be determined by those skilled in the art.

In suspension culture and adhesion culture, a known differentiation inducer can be used in combination. For example, when nerve progenitor cells are to be differentiation-induced from an embryonic stem cell, a known inducer of differentiation into nerve progenitor cells can be used in combination. Examples of such differentiation inducers include NGF [Biochem. Biophys. Res. Commun., 199, 552(1994)], retinoic acid [Dev. Biol., 168, 342(1995); J. Neurosci., 16, 1056(1996)], BMP inhibitory factor [Nature, 376, 333-336 (1995)], IGF [Genes & Development, 15, 3023-8 (2003)], Nodal inhibitor, Wnt inhibitor [Nature Neurosci. 8, 288-296 (2005)], Activin (Proc Natl. Acad. Sci. USA, 2005 Aug. 9; 102(32) 11331-6), and the like.

In the present invention, when laminin and entactin are used as a basement membrane reference standard, Nodal and Activin are desirably used as known differentiation inducers.

The amount of the differentiation inducer to be used in combination is not particularly limited and those of ordinary skill in the art can prepare a suitable amount that induces a desired differentiation. When Nodal and Activin are used for differentiation induction of retinal progenitor cells, Nodal is generally added to a culture solution at a concentration of 50 ng/mL-4000 ng/mL, preferably 200 ng/mL-2000 ng/mL, and Activin is generally added to a culture solution at a concentration of 20 ng/mL-2000 ng/mL, preferably 50 ng/mL-500 ng/mL. The culture solution is desirably exchanged daily. By adding a differentiation inducer besides the above-mentioned basement membrane reference standards when performing a floating culture of aggregates, the differentiation induction method to be described below can be performed further efficiently.

The timing of addition of a differentiation inducer is not particularly limited, and it may be added from the initial stage of differentiation induction or at a suitable time point. When Nodal and Activin are used for the above-mentioned object, they may be added one day after the start of the culture and continuously added for 7 to 10 days thereafter.

Figure 3:
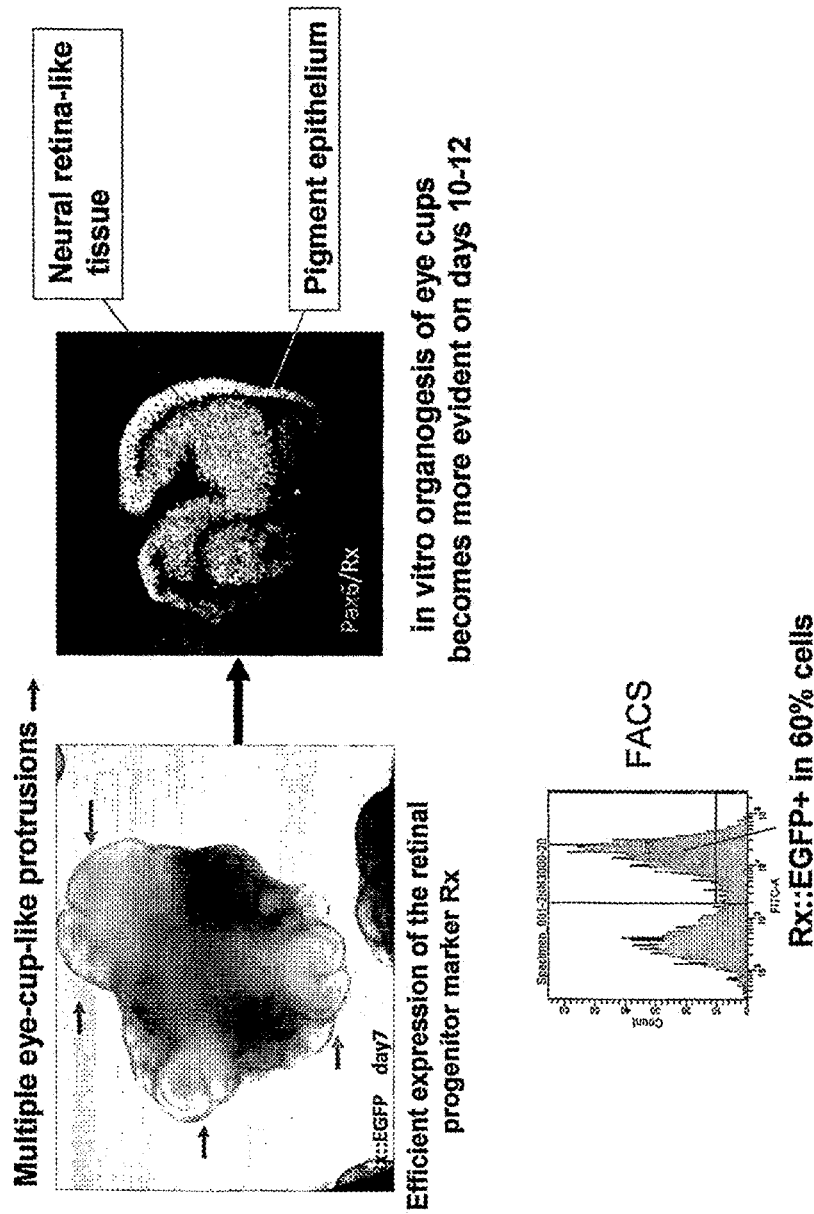
FIG. 3 shows that a plurality of optic cup-like tissues are self-formed in an aggregate of mouse ES cells obtained by the modified SFEBq method.

According to the above-described suspension culture method and combination of suspension culture and adhesion culture, nerve progenitor cells can be obtained from a stem cell by setting duration of cultivation and the like as appropriate. Particularly in the step (2), when homogenous aggregates of stem cells are suspension-cultured in the presence of a basement membrane reference standard for several days to several tens of days (e.g., 7 to 12 days for mouse ES cells, 20 to 40 days for human ES cells), self-formation of a plurality of optic cup-like protrusion structures as shown in FIG. 3 (hereinafter, this structure is described as "optic cup-like tissue") is observed in the aggregate of stem cells [hereinafter, of the step (2), particularly the step of allowing an optic cup-like tissue to be self formed in the aggregate is described as "step (2')"].

The identity of the retinal progenitor cells obtained by the above-described suspension culture method or combination of suspension culture and adhesion culture can be confirmed by the presence or absence of the expression of a marker gene and the like or the shape and the like of the cells or tissue as an index, which may be combined as required. Choice of marker gene for retinal progenitor cells and how to analyze their expression are as described in (2) above.

The thus-obtained optic cup-like tissue not only simply morphologically has an optic cup-like protrusion in the aggregate, but also exhibits a high level of expression of the retinal progenitor cell marker Rx from the cells constituting the tissue. Also observed in the outer part of the protrusion is a layer of retinal pigment epithelial cells that express Pax6. This structure of optic cup-like tissue is extremely similar to the structure of optic cup tissue in the genesis of a living organism. Therefore, according to the method of the present invention, it is possible to produce not only nerve progenitor cells (preferably retinal progenitor cells), but also a self-assembled optic cup-like tissue, from a stem cell.

Because the optic cup-like tissue obtained is self-formed as a protrusion from the aggregate, it is possible to obtain a highly pure mass of retinal progenitor cells by separating the protrusion. Accordingly, the present invention provides a method of separating or identifying a mass of retinal progenitor cells, comprising the above-described steps (1) and (2').

A mass of retinal progenitor cells can be obtained by cutting out the self-formed optic cup-like tissue from the aggregate physically and morphologically. Therefore, this method makes it possible to easily separate the mass of retinal progenitor cells. Because this method obviates the operation of confirming the position of retinal progenitor cells using a retinal progenitor cell marker and the like in obtaining the retinal progenitor cells by suspension-culturing aggregates of stem cells, a mass of retinal progenitor cells can easily be obtained by merely cutting out the cell mass formed as a protrusion in the aggregate.

(3-3) The Step of Suspension-Culturing the Formed Optic Cup-Like Tissue in Organ Culture Broth [Step (3)]

This is a step wherein the optic cup-like tissue obtained in the step (2') is suspension-cultured in an organ culture broth.

In this step, the optic cup-like tissue self-formed in the step (2') is suspension-cultured in an organ culture broth. The optic cup-like tissue used may be the aggregate of stem cells containing the optic cup-like tissue; the optic cup-like tissue formed as a protrusion from the aggregate of stem cells may be cut out physically and morphologically, and this may be suspension-cultured in an organ culture broth. When the optic cup-like tissue has been cut out, the entire aggregate of stem cells can be handled as a mass of Rx-positive retinal progenitor cells; therefore, it is possible to induce the differentiation of retinal progenitor cells more efficiently to produce retinal tissue and retinal layer-specific neurons.

The optic cup-like tissue can be cut out using any method; it is possible to cut out the tissue from an aggregate of stem cells using microtweezers and the like.

While the organ culture broth used to culture the optic cup-like tissue is not particularly limited, an organ culture broth in common use for induction of retinal cells is preferably used. Examples include (1) DMEM/F12/N2+0.5 µM retinoic acid, (2) 66% E-MEM-HEPES+33% HBSS+1% FCS+N2 supplement+5.75 mg/ml glucose+200 mM L-glutamine+20 ng/ml aFGF+20 ng/ml bFGF+20 nM Shh+1 mM retinoic acid+100 mM taurine, or (3) G-MEM+5% KSR+N2 supplement+0.1 mM non-essential amino acids+1 mM pyruvate+0.1 mM 2-mercaptoethanol+1 mM retinoic acid+100 mM taurine and the like.

The optic cup-like tissue is cultured in an organ culture broth. The incubator used in the suspension culture of the optic cup-like tissue may be the same as the incubator used in the above-described step (2). Other culturing conditions such as culturing temperature, $CO_2$ concentration and $O_2$ concentration at the time of optic cup-like tissue suspension culture can be set as appropriate. The culture temperature is not particularly limited, and is, for example, about 30 to 40° C., preferably about 37° C. The $CO_2$ concentration is, for example, about 1 to 10%, preferably about 5%. Meanwhile, the $O_2$ concentration is, for example, 20 to 70%, preferably 20 to 60%, more preferably 30 to 50%, when retinal progenitor cells are to be differentiation-induced, and taking into account the high oxygen requirement thereby.

The culturing time in this step is not particularly limited, and is normally 48 hours or more, preferably 7 days or more.

The optic cup-like tissue self-formed in the step (2') is self-induced to a retinal tissue through this step. Hence, by suspension-culturing the optic cup-like tissue self-formed in the step (2') in an organ culture broth, a retinal tissue or a cell population constituting the retinal tissue is self-induced in vitro. Accordingly, the present invention provides a method of producing a retinal tissue in vitro by self formation of retinal tissue and a method of producing a cell population constituting the retinal tissue. Here, "in vitro" merely refers to being not in a living organism.

Figure 4:
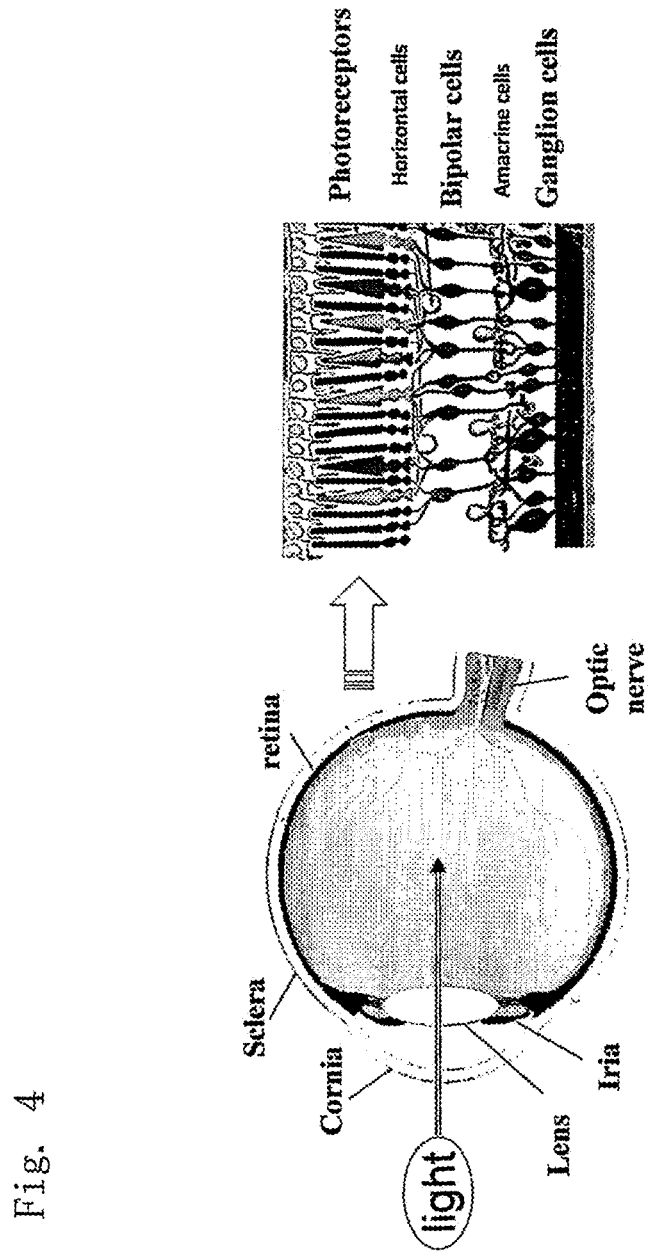
FIG. 4 is a schematic diagram of the living retina.

As shown in FIG. 4, the retinal tissue in a living organism has a structure wherein nerve cells are orderly arranged in a regular five-layer laminar structure so as to allow the incidental light through the cornea and lens to be received by surface photoreceptor cells and converted to an electric signal, to transmit information in the order of bipolar cells and nerve ganglion cells, and to finally transmit the signal to the cerebrum. The retinal tissue self-formed by the method of the present invention is not a mere assembly of retinal cells, but surprisingly has a structure that is morphologically extremely similar to the living retinal tissue.

The retinal tissue self-formed by the present invention has a self-formed five-laminar structure of nerve cells in regular arrangement in the same order as in the retinal tissue of a living organism. The five layers are configured by different types of retinal cells (photoreceptor cells, horizontal cells, bipolar cells, amacrine cells, ganglion cells); by assuming this structure, the retinal tissue is capable of transmitting light stimuli from outside of the body to the central nervous system as electric stimuli.

According to the present invention, a method of selective differentiation induction from a stem cell to a cell population constituting this retinal tissue, i.e., "retinal layer-specific neuron", is provided. Also provided is a method of producing "a retinal layer-specific neuron" from a stem cell.

The retinal layer-specific neuron thus obtained may be kept as it is or dispersion-treated (e.g., trypsin/EDTA treatment), and the cells may be further cultured under adhesive conditions. In adhesion culture, it is preferable that a cell-adhesive incubator, for example, an incubator coated with an extracellular matrix and the like (e.g., poly-D-lysine, laminin, entactin, fibronectin), be used. Culturing conditions for the adhesion culture, such as culturing temperature, $CO_2$ concentration, and $O_2$ concentration, can easily be determined by those skilled in the art. In this operation, the cells may be cultured in the presence of a known differentiation inducer. Examples of such differentiation inducers include NGF [Biochem. Biophys. Res. Commun., 199, 552(1994)], retinoic acid [Dev. Biol., 168, 342 (1995); J. Neurosci., 16, 1056(1996)], BMP inhibitory factor [Nature, 376, 333-336 (1995)], IGF [Genes & Development, 15, 3023-8 (2003)] and the like.

The thus-obtained retinal tissue and retinal layer-specific neuron can be identified by the presence or absence of the expression of a marker gene and the like as an index, which may be combined as required. The retinal layer-specific neuron obtained can also be identified by examining the morphology of the cells. Furthermore, on the basis of these marker expression patterns or cell morphology, it is also possible to isolate desired particular cells.

The expression of a marker gene can be confirmed by performing quantitative PCR as described in (2) above. Alternatively, the identity may be confirmed by the expression of GFP and the like by manipulating the cells to allow a desired marker gene to be expressed as a fusion protein of a marker gene product and GFP or the like. The expression of the protein may be detected using an antibody specific for a marker gene product.

Examples of useful marker genes include, but are not limited to, publicly known markers such as Rx (retinal progenitor cells), PAX6 (retinal progenitor cells), nestin (expressed in hypothalamic neuron progenitor cells, but not in retinal progenitor cells), Sox1 (expressed in hypothalamic nerve epithelium, but not in the retina), Crx (photoreceptor cell progenitor cells), Chx10 (bipolar cells and juvenile retinal progenitor cells), L7 (bipolar cells), Tuj1 (ganglion cells), Brn3 (ganglion cells), calretinin (amacrine cells), calbindin (horizontal cells), rhodopsin (photoreceptor cells), recoverin (photoreceptor cells), RPE65 (pigment epithelial cells), and Mitf (pigment epithelial cells). By combining as appropriate the presence and absence of the expression of these marker genes, the cells obtained can be identified. For example, amacrine cells are positive for both calretinin and Pax6 and negative for Tuj1, as stated above. Retinal ganglion cells are positive for both Brn3 and Tuj1.

(4) Culture Products

The present invention also provides culture products as obtained by the method of the present invention. The culture products of the present invention can include all of the cell culture products obtained by the method of the present invention, such as a suspended aggregate of stem cells, cells obtained by dispersion-treating a suspended aggregate, and cells obtained by culturing dispersion-treated cells.

The culture products of the present invention also include homogenous cells and assembled cell populations isolated and purified from the above-described culture products to the extent of acceptable administration to subjects, for example, nerve progenitor cells (e.g., retinal progenitor cells) and the like obtained via the steps (1) and (2), optic cup-like tissue, a mass of retinal progenitor cells obtained via the steps (1) and (2'), or retinal tissue, retinal layer-specific neuron and the like obtained via the steps (1), (2') and (3).

The culture products of the present invention can be used as therapeutic drugs for diseases based on disorders of nervous system cells (e.g., retinal cells), as replenishers of cells and tissues injured by other causes (e.g., for use in transplantation surgery), and for other purposes.

Examples of diseases based on disorders of nervous system cells include Parkinson's disease, spinocerebellar degeneration, Huntington chorea, Alzheimer's disease, ischemic cerebral diseases (e.g., cerebral stroke), epilepsy, brain traumas, spinal injuries, motor nerve diseases, neurodegenerative diseases, cochlear hearing loss, multiple sclerosis, amyotrophic lateral sclerosis, diseases caused by neurotoxic disorders, and the like. In particular, diseases based on retinal cell disorders include, for example, pigmentary degeneration of the retina, senile macular degeneration, glaucoma, diabetic retinopathy, neonatal retinopathy, and retinal artery obstruction. The culture products of the present invention can also be used to supplement cells and tissues lost due to ophthalmologic surgery (e.g., after retinoplasty for retinal detachment) and the like (e.g., retinal transplantation surgery).

When using cells obtained by the method of the present invention (e.g., nerve progenitor cells) as a therapeutic drug for a disease based on a disorder of the cells, it is preferable that the cells be transplanted to the subject after increasing the purity of the cells.

Any method of cell separation in public knowledge can be used for cell purification. Such methods include, for example, a method using a flow cytometer [see, for example, Antibodies—A Laboratory Manual, Cold Spring Harbor Laboratory (1988), Monoclonal Antibodies: principles and practice, Third Edition, Acad. Press (1993), Int. Immunol., 10, 275 (1998)], the panning method [see, for example, Monoclonal Antibodies: principles and practice, Third Edition, Acad. Press (1993), Antibody Engineering, A Practical Approach, IRL Press at Oxford University Press (1996), J. Immunol., 141, 2797 (1988)], and cell fractionation based on sucrose density differences [see, for example, Soshiki Baiyou no Gijyutsu (3rd edition), Asakura Shoten (1996)].

The method of the present invention for increasing cell purity comprises the step of culturing cells obtained by differentiation-inducing the above-described stem cells (e.g., nerve progenitor cells) in a medium containing an anticancer agent. Thereby, undifferentiated cells can be removed, making it possible to obtain differentiated cells of higher purity, which are more suitable for pharmaceutical use. Hence, by a treatment with an anticancer agent, cells other than desired differentiated cells, for example, undifferentiated cells, can be removed.

Here, the anticancer agent is exemplified by mitomycin C, 5-fluorouracil, adriamycin, Ara-C, methotrexate and the like. These anticancer agents are preferably used at concentrations that are more cytotoxic to undifferentiated cells than to differentiation-induced cells. Specifically, cultivation with these anticancer agents may be performed in accordance with the above-described procedures of cultivation to determine optimum concentrations. For example, a method is useful wherein cells are cultured in a $CO_2$ incubator aerated with 5% gaseous carbon dioxide at 37° C. for several hours, preferably for 2 hours, using a medium containing these anticancer agents at concentrations one-hundredth to 1 time the range of concentrations for living organisms specified in the Japanese Pharmacopoeia.

Any medium allowing cultivation of the differentiation-induced cells can be used here. Specifically, the aforementioned media and the like are useful.

In transplantation therapy, graft rejection due to histocompatibility antigen differences is often problematic, which problem, however, can be solved by using a stem cell having the nucleus of a somatic cell transplanted thereto, or a stem cell having a modified gene on the chromosome thereof.

By inducing differentiation using a stem cell having the nucleus of a somatic cell transplanted thereto, nerve progenitor cells, retinal progenitor cells, nervous system cells, retinal layer-specific neurons and the like of the individual which is the donor of the somatic cell can be obtained. Cells of such an individual are not only effective in transplantation medicine as they are, but also useful as a diagnostic material for determining whether an existing drug is effective on the individual. Furthermore, by culturing differentiation-induced cells for a long period, it is possible to determine their susceptibility to oxidative stress and senescence. By comparing their functions or life span with those of cells from other individuals, it is possible to evaluate the individual risks of contracting neurodegenerative and other diseases. These evaluation data are useful in providing an efficient prophylactic method for diseases diagnosed as developing at high incidences in the future.

Cells differentiation-induced from a stem cell by the method of the present invention, for example, nerve progenitor cells, retinal progenitor cells, nervous system cells, retinal layer-specific neurons and the like can be transplanted to a diseased site of a patient by a method known per se [see, e.g., Nature Neuroscience, 2, 1137(1999)].

(5) Formation of Retinal Nerve Network

The present invention provides a method of allowing a retinal nerve network to be self-formed in vitro, comprising the steps (1), (2') and (3). According to this method, it is possible to allow a cell aggregate obtained by the modified SFEBq method to form a retinal nerve network therein without becoming a disarrayed nerve cell mass.

The construction of a retinal nerve network in the in vitro cell aggregates can be confirmed by, for example, observing electrical excitement by light stimulation [Homma et al., (2009), J. Neurosci. Res. 87(9)2175-2182] or imaging analysis with calcium release as an index. Here, "in vitro" refers to being not in a living organism.

In the retinal nerve network self-formed by the method of the present invention, an elevation of $Ca^{2+}$ (calcium oscillation) synchronized or non-synchronized with surrounding cells is repeatedly observed in many cells. Hence, the retinal nerve network formed by the method of the present invention preferably can be accompanied by a synchronized spontaneous firing. Here, "firing" refers to an excitatory activity due to depolarization of nerve cells, and "spontaneous firing" refers to the spontaneous occurrence of the firing. Hence, the retinal nerve network formed by the method of the present invention can cause nerve activities similar to the living retina in a certain aspect.

Provided according to the present invention is a culture product as obtained by the method of the present invention, specifically a cell aggregate that constitutes the above-described retinal nerve network. This culture product (cell aggregate) has formed a retinal nerve network that is extremely similar to the retinal nerve network in a living organism, so that it can be used for screening for therapeutic drugs for diseases based on disorders of nervous system cells, for example, retinal cells, screening for therapeutic drugs for cell injuries due to other causes, or toxicity tests thereof and the like. Here, examples of diseases based on disorders of retinal cells include organic mercury poisoning, chloroquine retinopathy, pigmentary degeneration of the retina, senile macular degeneration, glaucoma, diabetic retinopathy, neonatal retinopathy, and the like.

This culture product (cell aggregate) can also be used as a therapeutic drug for diseases based on retinal cell disorders, a therapeutic drug for cell injuries due to other causes and the like.

(6) Formation of Retinal Tissue Structure

The present invention provides a method of allowing the steric structure of retinal tissue to be self-formed in vitro, comprising the steps (1), (2') and (3). According to this method, it is possible to form the steric structure of retinal tissue in a cell aggregate obtained by the modified SFEBq method without becoming a disarrayed nerve cell mass. More preferably, it is possible to mimic the initial process of retinal histogenesis with ongoing self-assembly in the same sequence as the retinal formation found in the optic cup primordium.

The self formation of the steric structure of retinal tissue in the cell aggregate in vitro can be confirmed by, for example, the expression of layer-specific retinal cell markers such as Chx10, Tuj1, caltetinin, calbindin, and rhodopsin, light or electron microscopic morphological analysis, live imaging of GFP-transferred cells and the like. Here, "in vitro" has the same meaning as the above.

According to the present invention, the culture product obtained by the method of the present invention, specifically an aggregate of cells constituting the steric structure of retinal tissue is provided. The culture product of the present invention has a structure that is morphologically extremely similar to the living retina, so that it can be used for screening for therapeutic drugs for diseases based on disorders of nervous system cells, particularly retinal progenitor cells and retinal cells, screening for therapeutic drugs for cell injuries due to other causes, or toxicity tests thereof and the like. Here, diseases based on disorders of retinal progenitor cells or retinal cells include, for example, organic mercury poisoning, chloroquine retinopathy, pigmentary degeneration of the retina, senile macular degeneration, glaucoma, diabetic retinopathy, neonatal retinopathy, and the like.

(7) Screening Method

The present invention provides a test substance screening method comprising using a culture product of the present invention. Particularly, a culture product of the present invention has an already formed nerve network that is extremely similar to the living nerve network, and also has an already formed retinal tissue that is extremely similar to the histogenetic protrusion of the retina, so that it can be applied for screening for therapeutic drugs for diseases based on disorders of nervous system cells, for example, retinal progenitor cells and retinal cells, screening for therapeutic drugs for cell injuries due to other causes, or toxicity tests thereof, and development of a new therapeutic method for diseases of nervous systems and the like.

Here, "a test substance" is exemplified by substances whose efficacy as therapeutic drugs for diseases of nervous systems is to be determined and substances that are therapeutic drugs for other diseases whose influences (e.g., toxicity) on nerves must be determined. The substance may be any one of low-molecular compounds, high-molecular compounds, proteins, nucleic acids (DNA, RNA and the like), viruses and the like. Such substances can be chosen as appropriate by those skilled in the art.

The present invention is hereinafter described in more detail by means of the following Comparative Examples and Examples, which, however, are for illustrative purposes only and never limit the scope of the invention.

EXAMPLES

Comparative Example 1: Highly Efficient Differentiation Induction into Cerebral Cortex Progenitor Cells by the SFEBq Method (Method)

EB5 cells of mouse ES cells (E14-derived) or cells of an E14-derived cell line wherein the Venus gene, which is a modified GFP (green fluorescent protein), had been knocked in the cerebral nerve marker Bf1 gene as a nerve differentiation reporter by homologous recombination (hereinafter described as "Bf1/Venus-mES cells") were cultured as described in the literature (Watanabe et al., Nature Neuroscience, 2005), and used in the experiments.

The medium for maintenance culture used was G-MEM medium (Invitrogen) supplemented with 1% fetal calf serum, 10% KSR (Knockout Serum Replacement; Invitrogen), 2 mM glutamine, 0.1 mM non-essential amino acids, 1 mM pyruvic acid, 0.1 mM 2-mercaptoethanol and 2000 U/ml LIF. For nerve differentiation induction by suspension culture, ES cells were mono-dispersed using 0.25% trypsin-EDTA (Invitrogen), and suspended in 150 µl of differentiation medium on a non-cell-adhesive 96-well culture plate (SUMILON Spheroid plate, Sumitomo Bakelite Co., Ltd.) at $3 \times 10^3$ cells per well to allow aggregates to be formed quickly, after which the plate was incubated at 37° C., 5% $CO_2$ for 7 days (SFEBq method; FIG. 1A).

The differentiation medium used in this operation was a serum-free medium prepared by adding 10% KSR, 2 mM glutamine, 1 mM pyruvate, 0.1 mM non-essential amino acids, 0.1 mM 2-ME, 250 µg/ml recombinant human Dkk-1, and 1 µg/ml recombinant human Lefty-1 to G-MEM medium (see Watanabe et al., Nature Neuroscience, 2005).

Figure 1H:
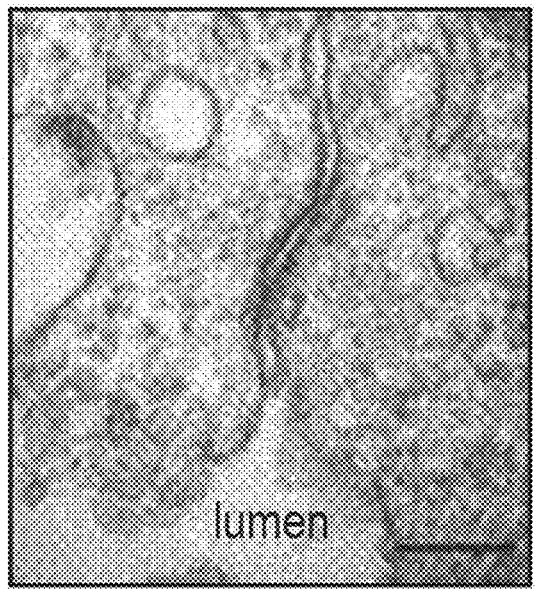
Figure 1I:
Figure 1J:
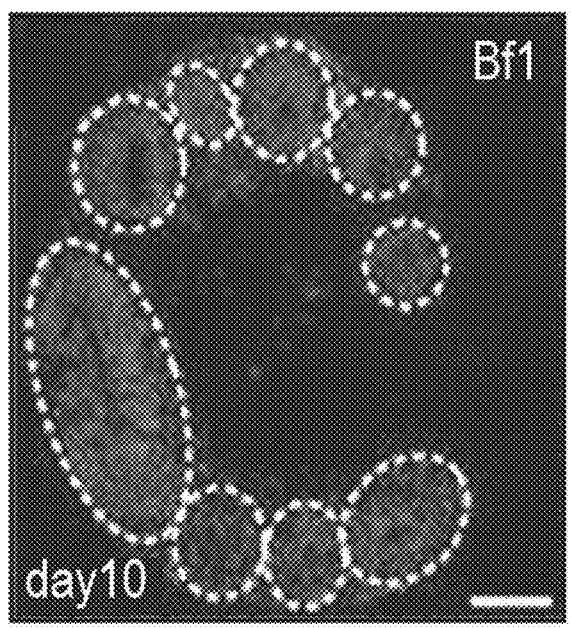
Figure 1K:
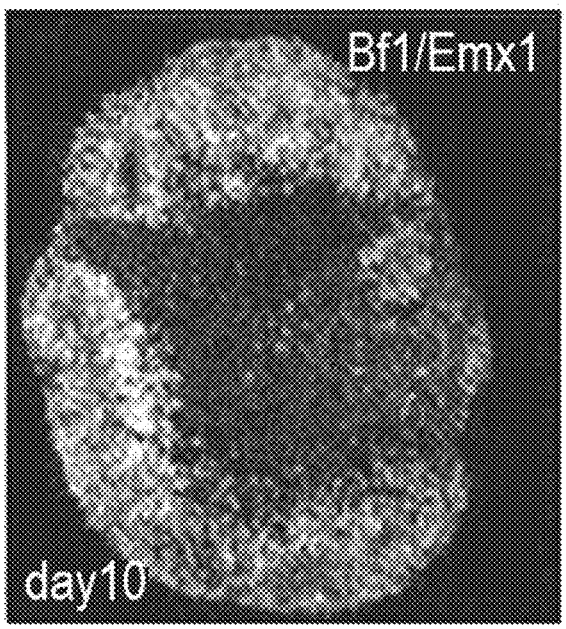
Figure 1L:
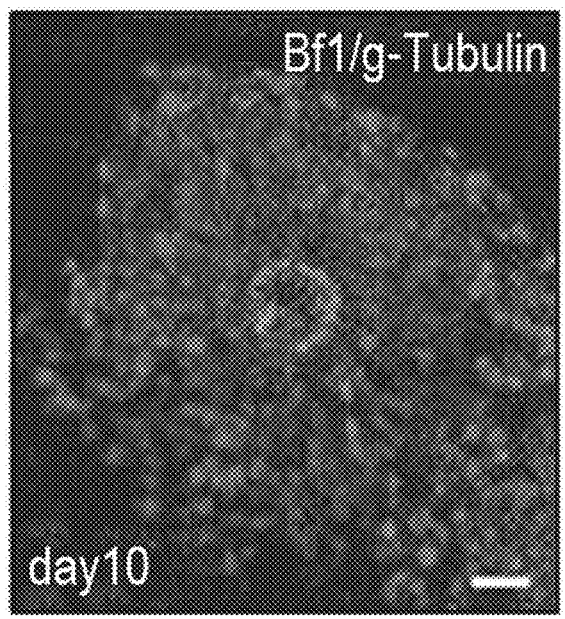
Figure 1M:
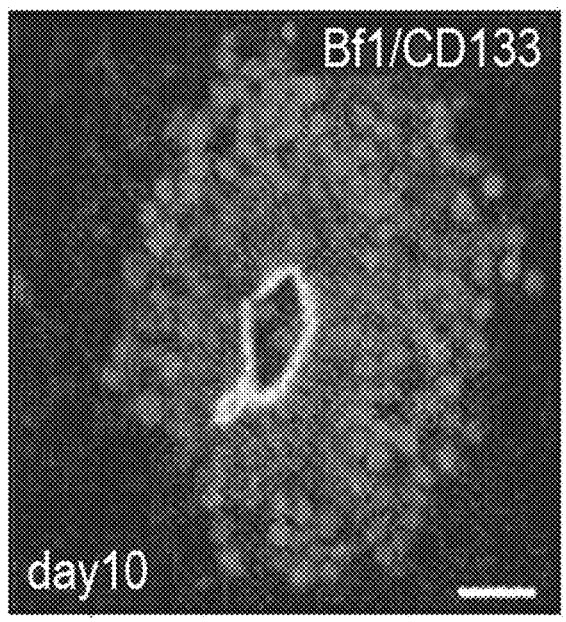
Figure 1N:
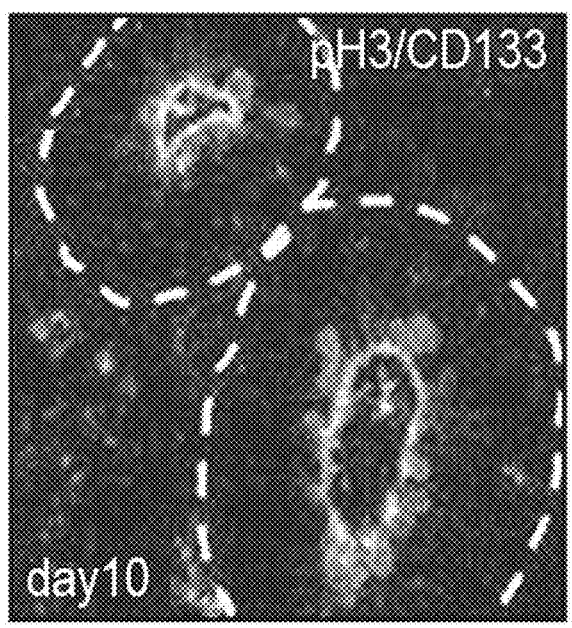
Figure 1O:
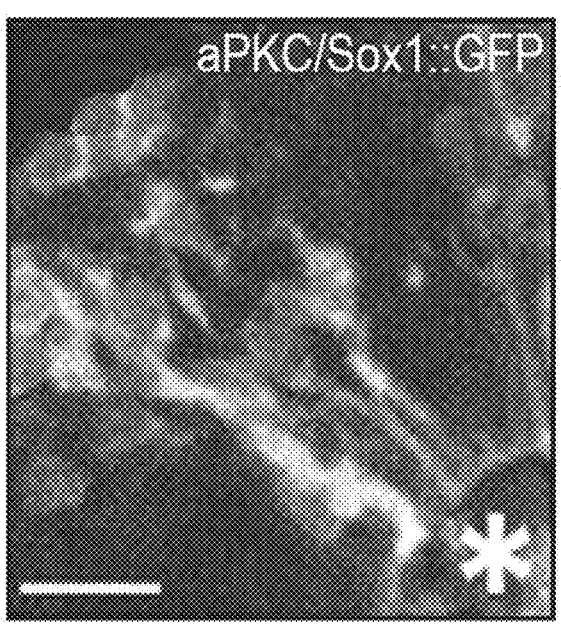

The aggregate masses were recovered in a 6 cm non-adhesive plastic dish (3.5 ml of differentiation medium), and continued to be suspension-cultured for 3 days (10 days in total), after which the differentiation status was analyzed by fluorescent immunostaining. The results are shown in FIGS. 1A-1O.

(Results)

Immunostaining analysis revealed that 10 days after the start of differentiation culture, about 70% of the cells in the aggregate expressed the cerebrum-specific marker Bf1, with 90% of the Bf1-positive cells expressing the cerebral cortex-specific marker Emx1. Also when differentiated Bf1/Venus-mES cells were analyzed by the expression of Venus-GFP, about 70% of the cells were positive, the majority of which expressed Emx1 (FIG. 1A). Hence, the SFEBq method enables cerebral cortex cells (progenitor cells) to be differentiation-induced with high efficiency when using the above-described differentiation medium. When using a conventional method wherein aggregates of ES cells are gradually formed using a 10 cm culture dish (Watanabe et al., Nature Neuroscience, 2005), Bf1-positive cells accounted for up to 30%, of which less than 40% became positive for cerebral cortex marker Emx1. The presence of an epithelium-like structure with polarity in the aggregates was confirmed by the expression of N-cadherin (Ncad), CD-133, laminin and the like (FIG. 1B to G; Dapi shows nucleus), electron microscopic observation of the morphology of tight junction (FIG. 1H, parenthesized), adherence junction (FIG. 1I, parenthesized) and the like, rosette formation (FIG. 1J, FIG. 1K, dotted line indicates a rosette), the expression of polarity markers and differentiation markers (FIGS. 1L to O, dotted line indicates a rosette, asterisk indicates a lumen) and the like.

Hence, the SFEBq method, compared with the conventional method, promotes the differentiation of ES cells into the cerebrum, particularly into cerebral cortex, more efficiently.

Comparative Example 2: In Vitro Production of Cerebral Neurons from Cerebral Cortex Progenitor Cells Induced by the SFEBq Method (Method)

Aggregates obtained by continued differentiation culture for 12 days by the method described in Comparative Example 1 were enzymatically dispersed (SUMILON Neural Tissue Dissociation kit), seeded onto a culture plate coated with poly-D-lysine/laminin/fibronectin at $5 \times 10^4$ dells/cm², and cultured using DMEM/F12 medium supplemented with 1×N2 supplement and 10 ng/ml FGF2 for 2 days. Subsequently, the cells were further cultured using Neurobasal medium (supplemented with B27 supplement)+ 50 ng/ml BDNF+50 ng/ml NT3 for 6 days. The properties of the differentiated neuron were analyzed by a fluorescent immunostaining method. The results are shown in FIGS. 2A-2F.

(Results)

Figure 2A:
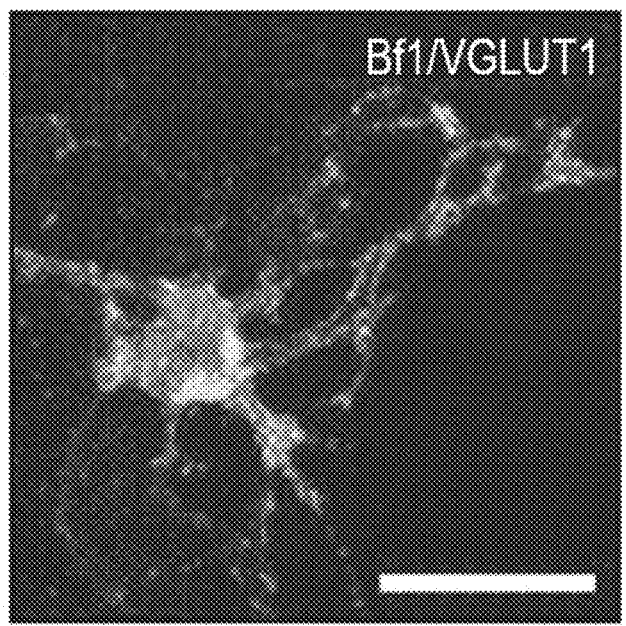
FIGS. 2A and 2C-2F show that aggregates of mouse ES cells obtained by the SFEBq method differentiate into cerebral cortex-specific neurons via cerebral cortex progenitor cells.
Figure 2B:
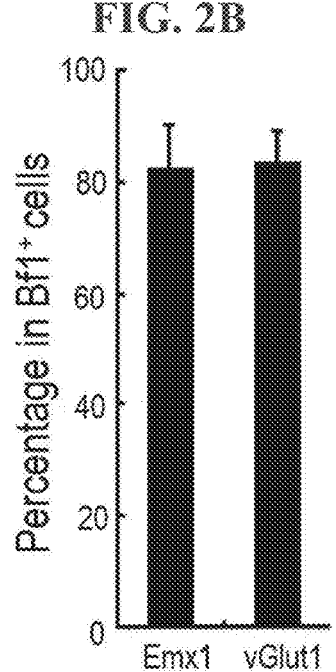
FIG. 2B is a graph showing the percentage of cells positive for cerebral cortex-specific marker Emx1 and positive for the glutamatergic neuron (abundantly present in cerebral cortex) marker VGluT1.
Figure 2C:
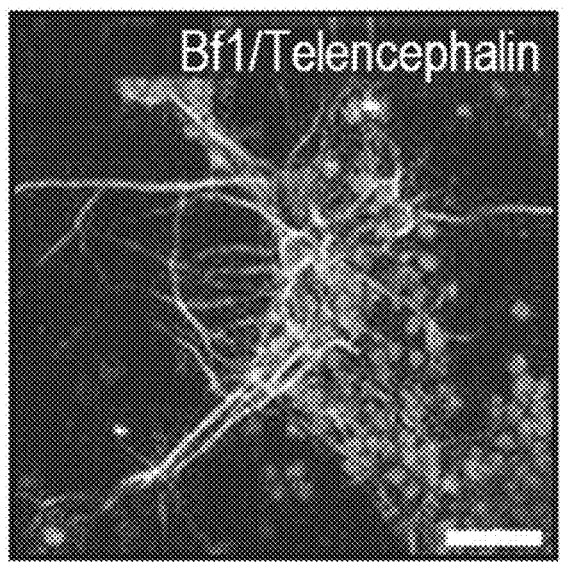
Figure 2D:
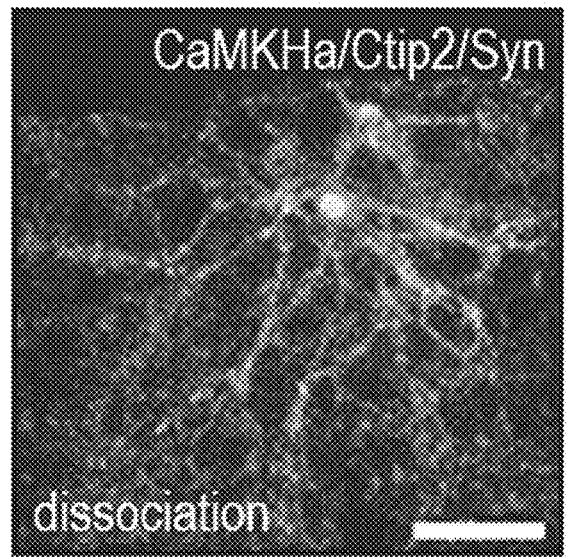
Figure 2E:
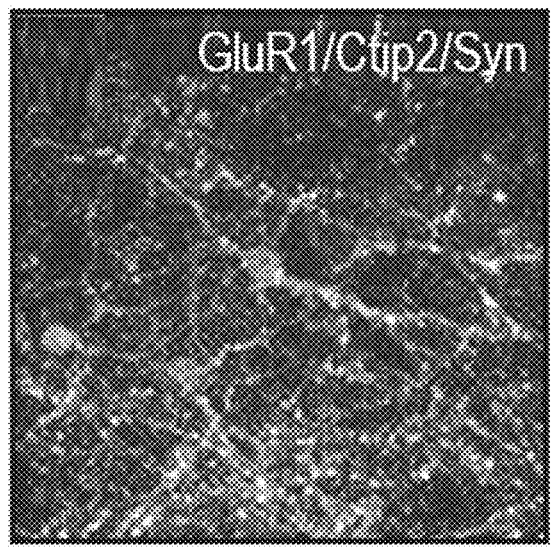
Figure 2F:
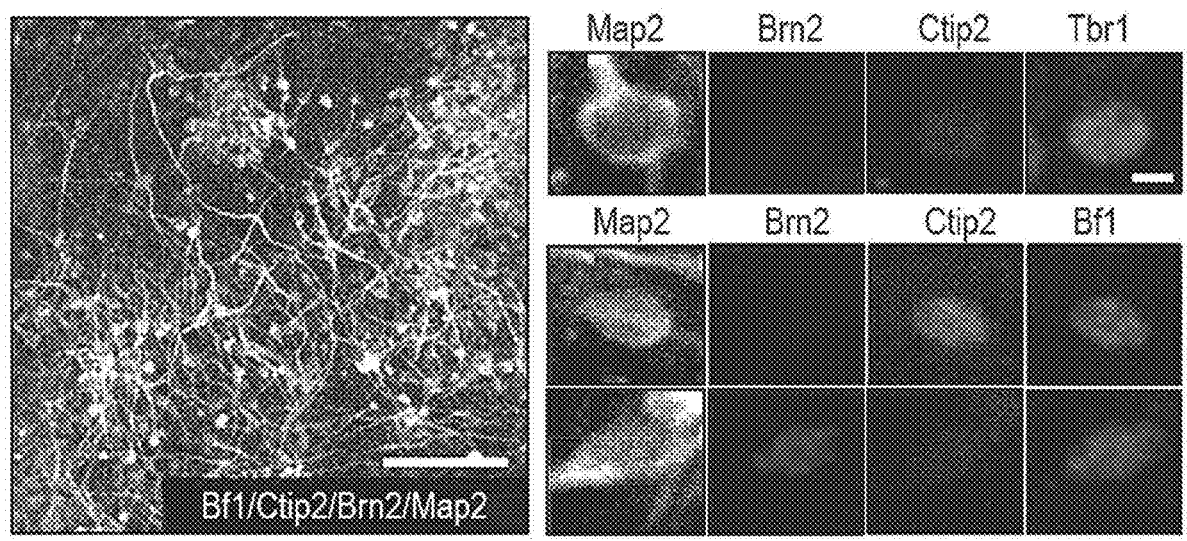

Most of the cells in the test tube became TuJ1-positive neurons, of which 80% were positive for the cerebral cortex-specific marker Emx1 and positive for the glutamatergic neuron (abundantly present in cerebral cortex) marker VGluT1 (FIGS. 2A to B). Also observed was the expression of a plurality of nerve markers characteristic of cerebral neuron (Telencephalin, GluR1, CamKII, Ctip2, Tbr1, Synapsin and the like) (FIGS. 2C to F).

Hence, differentiation of cerebral cortex progenitor cells induced by the SFEBq method into cerebrum-specific neuron was confirmed.

Example 1: Highly Efficient Differentiation Induction to Retinal Progenitor Cells by the Modified SFEBq Method with High Concentrations of Matrix Components Added and Optimized KSR Concentration (Method)

Rx-EGFP mES cells (mouse ES cells having EGFP knocked in at the early retinal progenitor cell marker gene Rx locus; Wataya et al, PNAS, 2008) were treated by the SFEBq method (a 96-well culture plate of low cell-binding ability) to quickly generate homogenous aggregates at 3000 cells per well, which were cultured for differentiation. The differentiation induction medium used here was G-MEM medium (Invitrogen), 2% KSR, 2 mM glutamine, 0.1 mM non-essential amino acids, 1 mM pyruvic acid and 0.1 mM 2-mercaptoethanol. Starting one day later, Matrigel was added to the medium in a ratio by volume of 1/100 to 1/25, and the cells were subjected to suspension aggregate culture for 7 days 5% $CO_2$, at 37° C. Subsequently, the cultivation was further continued under the nerve differentiation promoting conditions. Differentiation analysis was performed by the fluorescent immunostaining method (frozen sections) using the brain nerve progenitor marker Sox1, the cerebral marker Bf1, the retinal progenitor cell marker Rx, the neural retinal progenitor cell and bipolar cell marker Chx10, the photoreceptor cell marker rhodopsin antibody and the like.

(Results)

When using the medium comprising a 1/100 volume of Matrigel supplemented with 10% KSR as in Comparative Example 1, cerebral cortex progenitor cells expressing Bf1 were induced with constant efficiency (>50%; 9 days later). Meanwhile, when using the same medium but supplemented with 2% KSR under the same conditions, the expression of Bf1 decreased to less than 10%. With the 2% KSR medium comprising a 1/50 or 1/25 volume of Matrigel, the expression of Bf1 became less than 5%.

Conversely, in differentiation culture with a 2% KSR medium supplemented with Matrigel in a 1/100 volume or more, Rx-EGFP-positive and Rx antibody-positive cells emerged at 5% or more of the cells in the cell masses. With the addition of Matrigel in a 1/50 or 1/25 volume or more, about 60% of the cells became Rx-EGFP-positive. In differentiation culture with a 10% KSR medium supplemented with Matrigel in a 1/100 volume, the expression of Bf1 was less than 1%.

Example 2: Self Formation of Optic Cup-Like Tissue from Retinal Progenitor Cells Using the Modified SFEBq Method (Method)

The aggregates of Rx-positive cells obtained in Example 1 were cultured using a culture broth prepared by adding Matrigel in a 1/50 volume to 2% KSR medium for 7 days, after which it was transferred to a culture broth prepared by adding an N2 additive to the DMEM/F12 medium, and further suspension-cultured under 5% $CO_2$/40% $O_2$ conditions for 3 days.

(Results)

The strongly Rx-EGFP-positive portion formed a tissue as a protrusion from the cell mass (FIG. 3). Its histological profile was similar to that of the fetal optic cup (an early retinal tissue formed as a protrusion from the diencephalon), representing a structure wherein Rx-positive, Chx10-positive juvenile neural retinal tissue was wrapped by a layer of retinal pigment cells.

Example 3: Self Assembly of Retinal Tissue from Retinal Progenitor Cells Using the Modified SFEBq Method (Method)

Optic cup-like tissue as obtained in Example 2 (10 days of culture) was separated from the cell mass using microtweezers, and subjected to suspension culture with DMEM/F12/N2+0.5 µM retinoic acid (known to promote the survival of photoreceptor cells).

(Results)

Figure 5:
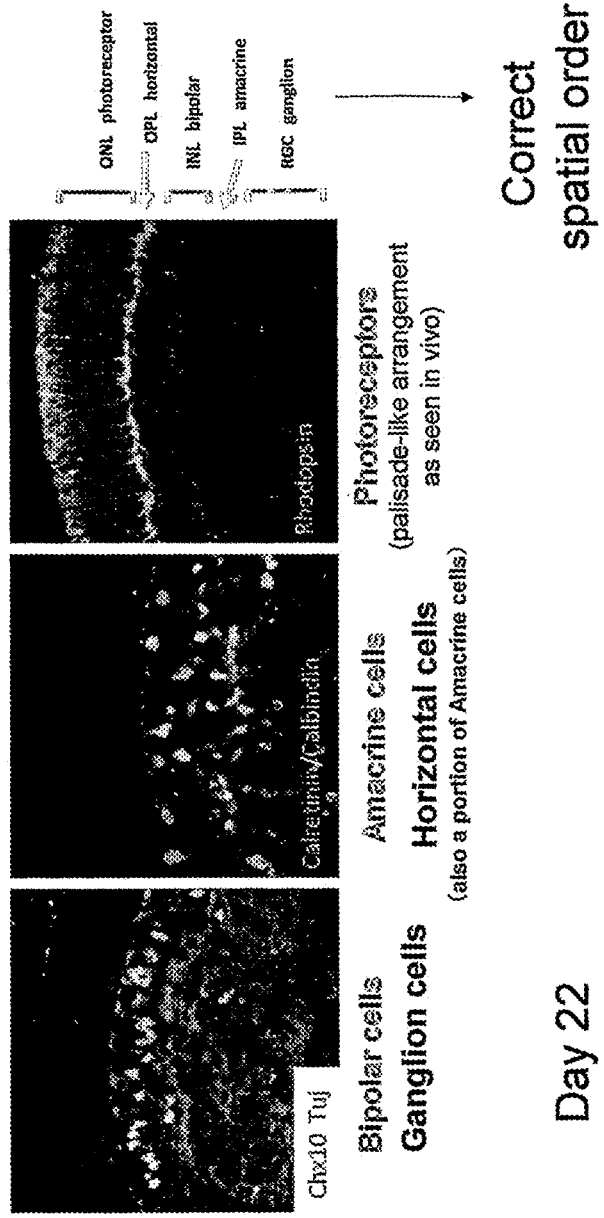
FIG. 5 shows that a retinal tissue is self-formed by suspension-culturing in an organ culture broth a mouse optic cup-like tissue self-formed by the modified SFEBq method.
Figure 6:
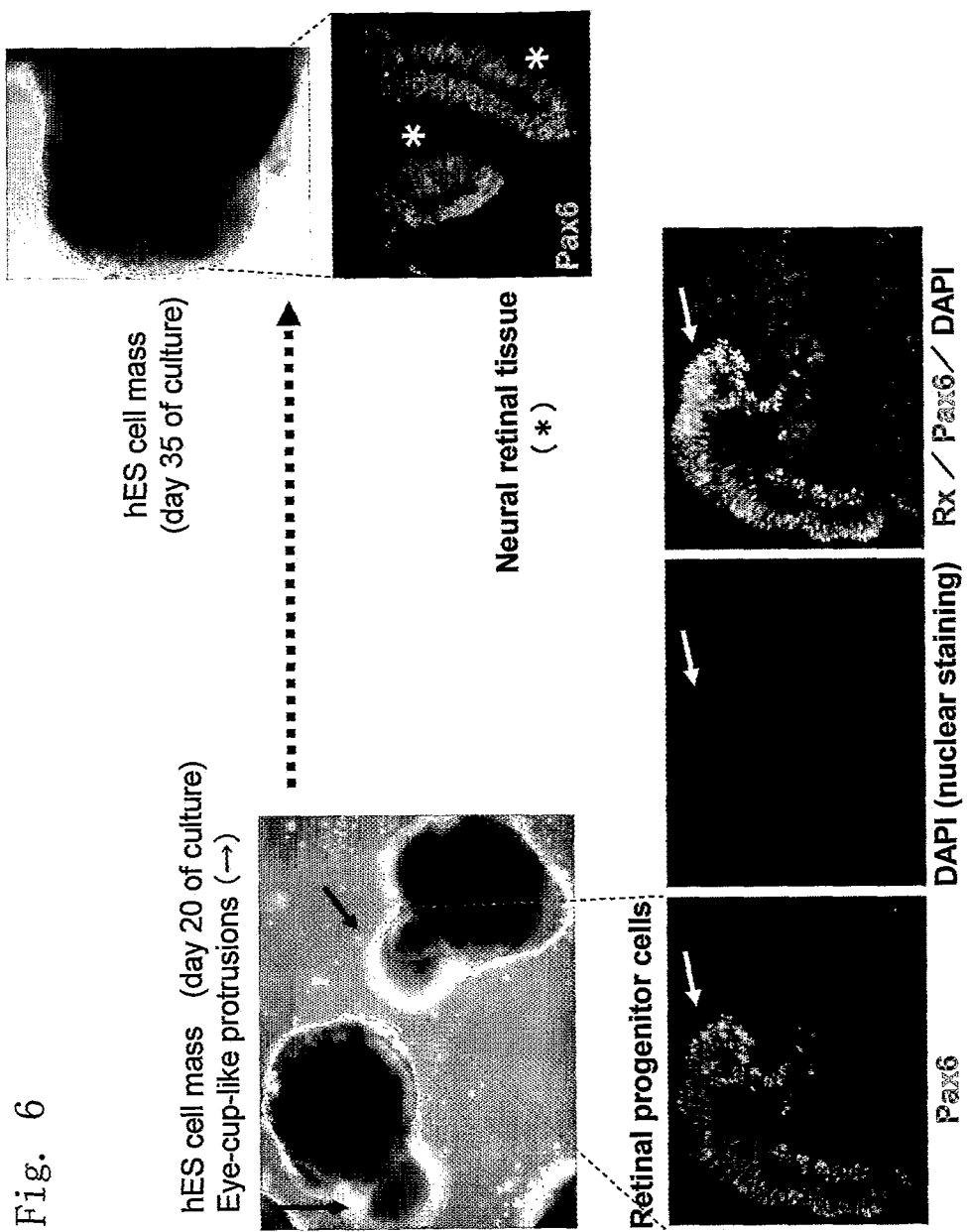
FIG. 6 shows a human optic cup-like tissue self-formed by the modified SFEBq method.

The suspension-cultured optic cup-like tissue had been induced to a laminar structure that is structurally extremely similar to the retina after birth (FIGS. 2A-2F and 3). Regularly formed in the outermost layer was a planar structure of photoreceptor cells (rhodopsin-positive and having an outer segment structure), possessing the right cell polarity. Under this layer were a layer of Chx10-positive bipolar cells and a layer of Calbindin-positive horizontal cells, under which a layer of Calretinin-positive/Pax6-positive/TuJ1-negative amacrine cells was present, and the lowermost layer was a layer of Brn3-positive/TuJ1-positive retinal ganglion cells, which were formed in an orderly manner (FIG. 5). The order of these layers corresponded to the retinal laminar structure in vivo. In summary, it has been shown that when applying the modified SFEBq method for suspension cell mass culture by the SFEBq method in consideration of the optimized combination of matrix treatment and medium, not only retinal progenitor cells are formed efficiently, but also a retinal tissue having a laminar structure is self-formed in vitro from these retinal progenitor cells.

Example 4: Electrophysiological Activities of Retinal Tissue Produced by the Modified SFEBq Method (Method)

Optic cup-like tissue was separated from the cell mass using microtweezers in the same manner as Example 3, and cultured with DMEM/F12/N2+0.5 µM retinoic acid. For electrophysiological examination, the tissue was cultured on a plate with multiple planar microelectrodes (MED probe); 2 days later, the action potentials of the axons emerging from the optic cup-like tissue were examined by the multipolar electrode field potential method (MED64; Alpha MED Scientific Inc.).

(Results)

The axons from the optic cup-like tissue were Tuj1-positive and thought to be derived from ganglion cells same as retinal tissue. A large number of spontaneous firings of irregular action potentials from these axons were observed by the multipolar electrode field potential method. These results confirmed that a network that induces spontaneous nerve activities, observed in juvenile retina of newborn babies in vivo and the like, had been formed in the optic cup-like tissue. It seems also possible to examine light-induced action potentials with MED 64 by the method of Homma et al. [Homma et al, (2009), J. Neurosci. Res. 87(9)2175-2182].

Example 5: Spontaneous Formation of Optic Cup-Like Protrusion Tissue from Human ES Cells (Method)

Human ES cells (khES1) were cultured for maintenance by an ordinary method (Ueno et al, PNAS 103, 9554-9559, 2006). The human ES cells were isolated from the plate by a method already in the public domain, and mono-dispersed with trypsin (Watanabe et al., Nature Biotech. 25, 681-686, 2007). These cells were quickly re-aggregated using a 96-well culture plate of low cell-binding ability in the same way as Comparative Example 1 and Example 1 to obtain homogenous aggregates. In that operation, the cells were suspended in a culture broth at 9000 cells per well of the 96-well plate. The culture broth used was DMEM/F12+10-20% KSR+2 mM glutamine+0.1 mM non-essential amino acids+0.1 mM 2-ME, with the addition of 10 µM of the Rock inhibitor Y-27632 (a cell death suppressant) during the first 6 days. Starting at 3 days of cultivation, Matrigel was added in a 1/100 volume, and the cells were cultured until day 18. Between day 18 and day 25, suspension culture was continued using DMEM/F12+N2+1 µM RA, with the $O_2$ concentration raised to 40%. Between day 25 and day 40, the cells were suspension-cultured in the presence of Neurobasal+B27+1 µM RA, 40% $O_2$.

(Results)

In the above-described cultivation, only when Matrigel was added, the formation of a continuous epithelial tissue of Rx-positive, Pax6-positive retinal progenitor cells was observed in a cell mass derived from a human ES cell. After 20 days of cultivation, as on day 7 of mouse ES cell culture, the formation of Rx-positive, Pax6-positive tissue as a protrusion from the main body of a cell mass derived from the human ES cell was confirmed. They comprised strongly Rx-positive neural retina progenitor tissue and weakly Rx-positive pigment epithelium progenitor tissue, both of which were nestin-negative. Also, 35 days later, the presence of Rx-positive, Pax6-positive, nestin-negative pseudostratified columnar epithelium tissue (a morphological characteristic of neural retina progenitor tissue) was confirmed.

Example 6: Efficient Induction of Retinal Epithelium in ES Cell Aggregates Using Purified Matrix Proteins and Nodal/Activin (Method)

Rx-GFP ES cells (3000 cells/well, 96-well plate) were cultured in SFEBq culture with G-MEM supplemented with 1.5% KSR. In this experiment, instead of adding Matrigel to culture, purified laminin and entactin (High concentration Laminin/Entactin complex; BD; 120 μg/ml) were added as extracellular matrix proteins on day 1 (24 hours after the onset of differentiation culture). Recombinant Mouse Nodal (R&D; 500-1000 ng/mL) or Human Activin (R&D; 250 ng/ml) was also added on day 1 and the Nodal treatment was continued until day 7. SFEBq aggregates were cultured for 7-10 days and the formation of RxGFP+ vesicles and cup structures were examined under a fluorescent microscope. Nodal and Activin are known to act on common cell surface receptors and activate Smad2/3 signals in the cell.

Figure 7:
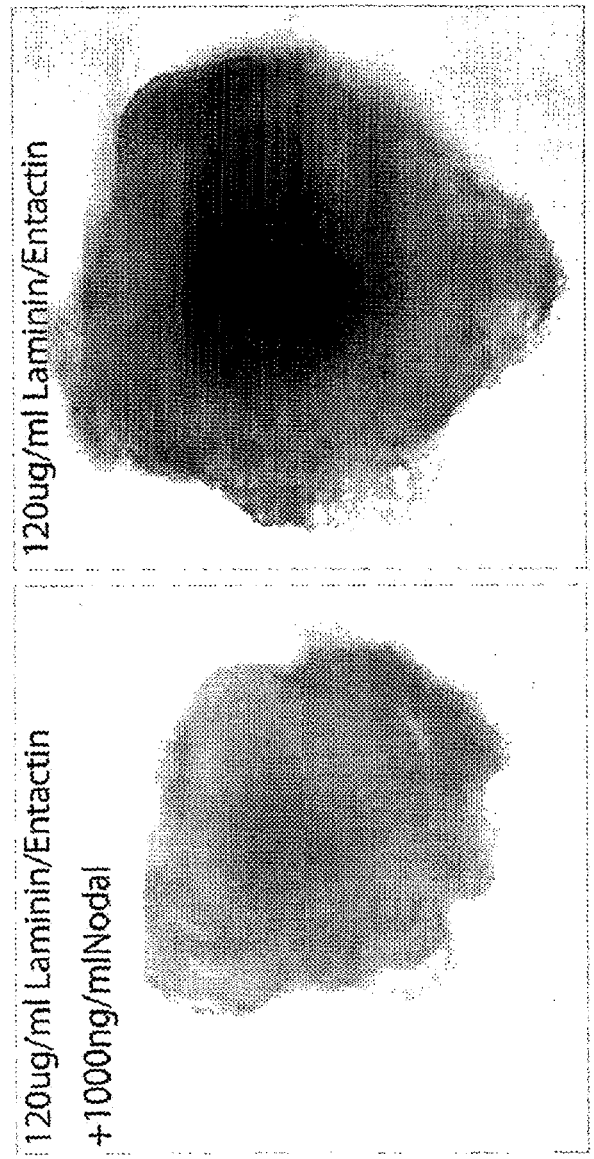
FIG. 7 shows a human optic cup-like tissue self-formed by the modified SFEBq method in the presence of purified laminin and entactin, and Nodal/Activin.

Results:

ES cells cultured without extracellular matrix proteins (Matrigel or laminin/entactin) or Nodal did not express Rx-GFP on days 7-10. Unlike 2% Matrigel, laminin+entactin alone did not induce Rx-GFP+ retinal epithelium on day 7 or 10. In contrast, when cells were treated with laminin+entactin and Nodal (both 500 and 1000 ng/ml) or Activin during days 1-7, large patches of Rx-GFP+ epithelia appeared in the SFEBq aggregates on day 7 (FIG. 7). They formed optic vesicle-like sacs on day 7 and later exhibited the optic cup-like morphology on day 10. TGF-beta1 or 2 (1000 ng/ml) did not replace the inducing activity of Nodal even when combined with laminin+entactin. Treatment of SFEBq cells with Nodal or Activin from day 0 inhibited both neural (Sox1) and retinal (Rx) differentiation in accordance with previous reports (Watanabe et al, Nature Neuroscience, 2005), indicating that the absence of Nodal/Activin signals at the initial phase of SFEBq culture is a preferred condition.

The three-dimensional retinal tissue formation can be induced by the defined matrix proteins laminin and entactin in the presence of Nodal.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

The contents disclosed in any publication cited herein, including patents and patent applications, are hereby incorporated in their entireties by reference, to the extent that they have been disclosed herein.

INDUSTRIAL APPLICABILITY

According to the method of the present invention, it is possible to efficiently differentiation-induce nervous system cells, thus allowing cytotherapy to be applied for neurodegenerative diseases. The method of the present invention also makes it possible to efficiently differentiation induction of diencephalon tissues (particularly retinal tissue), a task that has been difficult to achieve by the conventional method of differentiation, thus allowing cytotherapy to be applied for diseases associated with abnormalities of diencephalon tissues (particularly retinal tissue).

Furthermore, according to the present invention, the steric structure of retinal tissue having a retinal nerve network and a laminar structure can be produced in vitro. Therefore, the present invention is also of high utility in providing "tissue materials" that serve well in regenerative medicine, drug discovery and toxicity tests for the above-described pharmaceuticals and the like.

Another advantage of the present invention is that the risk in the transplantation of cells obtained by stem cell culture can be reduced to the risk levels in allotransplantation because it does not involve the use of an animal-derived cell as an inductor.

This application is based on a patent application No. 61/258,439 filed in United States, the contents of which are incorporated in full herein by this reference.

The invention claimed is:

1. A cell aggregate comprising Rx-positive cells and non-Rx-positive cells, and having been induced in vitro to differentiate from a mammalian pluripotent stem cell, wherein a portion comprising Rx-positive cells forms a protrusion from a main body of the cell aggregate, wherein the main body of the cell aggregate constitutes a non-retinal rest of the cell aggregate, wherein the protrusion comprises an optic cup-like structure, and wherein the non-retinal rest of the cell aggregate comprises cerebral tissue and is not diencephalon.

2. The cell aggregate according to claim 1, wherein the protrusion comprises Rx-positive and Chx10-positive juvenile neural retina tissue.

3. The cell aggregate according to claim 1, wherein the cell aggregate comprises a plurality of the protrusions.

4. The cell aggregate according to claim 1, wherein the protrusion comprises a continuous epithelial tissue of Rx-positive and Pax6-positive retinal progenitor cells.

5. The cell aggregate according to claim 1, wherein the protrusion comprises Rx-positive and Pax6-positive tissue.

6. The cell aggregate according to claim 1, wherein the protrusion comprises strongly Rx-positive neural retina progenitor tissue and weakly Rx-positive pigment epithelium progenitor tissue, both of which are nestin-negative.

7. The cell aggregate according to claim 1, wherein the non-retinal rest of the cell aggregate is non-Rx-positive.

8. An isolated retinal tissue aggregate comprising Rx-positive retinal progenitor cells, and having been induced in vitro to differentiate from a mammalian pluripotent stem cell, with a laminar structure which has a layer of Chx10-positive bipolar cells and a layer of Calbindin-positive horizontal cells under an outermost layer, and wherein the retinal tissue does not comprise diencephalon.

9. The retinal tissue aggregate according to claim 8, wherein a planar structure of photoreceptor cells, which is rhodopsin-positive and having an outer segment structure, is formed in the outermost layer, possessing a right cell polarity.

10. The retinal tissue aggregate according to claim 8, which has a layer of Calretinin-positive/Pax6-positive/TuJ1-negative amacrine cells under the layer of Calbindin-positive horizontal cells, and a lowermost layer is a layer of Brn3-positive/TuJ1-positive retinal ganglion cells, which are formed in an orderly manner.

11. A method of producing a mammalian retinal tissue with a laminar structure which has a layer of Chx10-positive bipolar cells and a layer of Calbindin-positive horizontal cells under an outermost layer, comprising the steps:
  (a) suspension-culturing, in a non-cell-adhesive culture vessel, mammalian pluripotent stem cells in a serum-free medium to form a homogenous mammalian aggregate of pluripotent cells,
  (b) suspension-culturing. in a non-cell-adhesive culture vessel. the homogenous mammalian aggregate of pluripotent stem cells formed in step (a) in the presence of a basement membrane preparation derived from Engelbreth Holm Swarn mouse sarcoma to allow an optic cup-like tissue to be self-formed in the homogenous mammalian aggregate of pluripotent cells, wherein the suspension culturing of step (b) is started 1 to 3 days after starting the suspension-culturing of step (a), (c) suspension-culturing the optic cup-like tissue formed in step (b) in an organ culture medium to allow a retinal tissue to be self-formed, thereby obtaining a cell aggregate of claim 1.

(d) separating the protrusion comprising optic cup-like structure from the cell aggregate of claim 1, and (e) subjecting the separated protrusion to suspension culture in an organ culture medium.

12. The method according to claim 11, wherein the organ culture medium comprises at least one of retinoic acid and taurine.

13. The method according to claim 12, wherein the organ culture medium further comprises N2 supplement.

* * * * *